United States Patent [19]
Ying et al.

[11] Patent Number: 5,657,760
[45] Date of Patent: Aug. 19, 1997

[54] APPARATUS AND METHOD FOR NONINVASIVE DOPPLER ULTRASOUND-GUIDED REAL-TIME CONTROL OF TISSUE DAMAGE IN THERMAL THERAPY

[75] Inventors: Hao Ying, League City; Craig J. Hartley, Houston, both of Tex.

[73] Assignee: Board of Regents, The University of Texas System, Austin, Tex.

[21] Appl. No.: 584,409

[22] Filed: Jan. 11, 1996

Related U.S. Application Data

[63] Continuation of Ser. No. 446,199, May 19, 1995, abandoned, which is a continuation of Ser. No. 237,348, May 3, 1994, abandoned.

[51] Int. Cl.$^6$ .................................................... A61B 8/00
[52] U.S. Cl. ................................... 128/660.03; 601/2
[58] Field of Search ............. 128/660.03, 661.07–661.1; 607/97; 601/2

[56] References Cited

U.S. PATENT DOCUMENTS

| | | | |
|---|---|---|---|
| 4,416,552 | 11/1983 | Hessember, Jr. et al. | 374/117 |
| 4,452,081 | 6/1984 | Seppi | 73/597 |
| 4,513,749 | 4/1985 | Kino et al. | 128/660.02 |
| 4,513,750 | 4/1985 | Heyman et al. | 128/660.02 |
| 4,576,177 | 3/1986 | Webster, Jr. | 128/660.03 |
| 4,800,899 | 1/1989 | Elliott | 607/156 |
| 4,887,605 | 12/1989 | Angelsen | 128/660.03 |
| 4,936,308 | 6/1990 | Fukukita et al. | 128/660.02 |
| 4,950,267 | 8/1990 | Ishihara | 606/12 |
| 5,050,597 | 9/1991 | Daikuzono | 607/89 |
| 5,154,707 | 10/1992 | Rink et al. | 606/12 |
| 5,163,432 | 11/1992 | Ueno et al. | 128/660.03 |
| 5,222,953 | 6/1993 | Dowlatshahi | 606/15 |

OTHER PUBLICATIONS

Amin et al., "Hepatic Metastases: Interstitial Laser Photocoagulation with Real–Time US Monitoring and Dynamic CT Evaluation of Treatment," *Radiology*, vol. 187, pp. 339–347 (May 1993).

Anzai, et al., "Nd:YAG Interstitial Laser Phototherapy Guided by Magnetic Resonance Imaging in an Ex Vivo Model: Dosimetry of Laser–MR–Tissue Interaction," *Laryngoscope*, vol. 101, pp. 755–760 (Jul. 1991).

Aretz, et al., "Intraluminal Guidance of Transverse Laser Coronary Atherectomy," *International Journal of Cardiac Imaging*, vol. 4, pp. 153–157 (1989).

(List continued on next page.)

*Primary Examiner*—Francis Jaworski
*Attorney, Agent, or Firm*—Arnold, White & Durkee

[57] ABSTRACT

A method and apparatus for noninvasive and real-time monitoring and feedback control of the extent and geometry of tissue damage induced by various thermal modalities (laser, electromagnetic wave, ultrasound and thermistor) in different thermal therapies (hyperthermia, thermal coagulation and ablation) is provided. Unlike the existing ultrasound configurations, which use non-Doppler ultrasound techniques, the single-beam configuration in this invention employs a multiple-range-gate pulsed Doppler technique. The configuration may be operated in A-mode, M-mode, or multi-dimensional image mode to monitor tissue thermal response in the tissue being treated at multiple tissue depths along the sound beam. By measuring changes in phase (i.e., motion) and amplitude (i.e., echogenicity) of the echoes returned from the tissue under treatment, the Doppler system can determine temporal and spatial profiles of tissue temperature and the extent and geometry of tissue thermal damage. The system can also differentiate tissue responses corresponding to coagulation of tissue (in hyperthermia or coagulation treatment) versus ablation of tissue. Further, the Doppler detection provides feedback signals using fuzzy logic technology to automatically and in real-time regulate thermal output of various thermal modalities so that optimal thermal treatment can be obtained. The control of thermal output is achieved by adjusting treatment parameters such as pulse rate, exposure time and output power in the case of lasers. The Doppler detection results can also be shown on a suitable display device to allow manual feedback control of a thermal modality by a human operator.

11 Claims, 27 Drawing Sheets

OTHER PUBLICATIONS

Aretz et al., "Ultrasound Guidance of Laser Atherectomy," *International Journal of Cardiac Imaging*, vol. 6, pp. 231–237 (1991).

Bihan et al., "Temperature Mapping with MR Imaging of Molecular Diffusion: Application to Hyperthermia," *Radiology*, vol. 171, pp. 853–857 (Jun. 1989).

Bleier, et al., "Real-Time Magnetic Resonance Imaging of Laser Heat Deposition in Tissue," *Magnetic Resonance in Medicine*, vol. 21, pp. 132–137 (1991).

Borst, et al., "Laser Ablation and the Need for Intra-Arterial Imaging," *International Journal of Cardiac Imaging*, vol. 4, pp. 127–133 (1989).

Crowley, et al., "Ultrasound Guided Therapeutic Catheters: Recent Developments and Clinical Results," *International Journal of Cardiac Imaging*, vol. 6, pp. 145–156 (1991).

Dachman et al.,"US–Guided Percutaneous Laser.Ablation of Laser Tissue in a Chronic Pig Model," *Radiology*, vol. 176, pp. 129–133 (1990).

Duda et al., "Ultrasound–Monitored Laser Angioplasty: Preliminary Clinical Results," *Cardiovasc. Intervent. Radiol.*, vol. 16, pp. 89–92 (1993).

Godlewski, et al., "Ultrasonic and Histopathological Correlations of Deep Focal Hepatic Lesions Induced by Stereotaxtic Nd–YAG Laser Applications," *Ultrasound in Med. & Biol.*, vol. 14, pp. 287–291 (1988).

Godlewski, et al., "Deep Localized Neodymium (Nd)–YAG Laser Photocoagulation in Liver Using a New Water Cooled and Echoguided Handpiece," *Lasers in Surgery and Medicine*, vol. 8, pp. 501–509 (1988).

Hartley, et al., "An Ultrasonic Method for Measuring Tissue Displacement: Technical Details and Validation for Measuring Myocardial Thickening," *IEEE Transactions on Biomedical Engineering*, vol. 38, pp. 735–747 (Aug. 1991).

Hartley, et al., "Doppler Quantification of Echo–Contrast Injections In Vivo," *Ultrasound in Med. & Biol.*, vol. 19, pp. 269–278 (1993).

Hashimoto, D., Takami, M., and Idezuki, Y., "In–Depth Radiation Therapy by YAG Laser for Maligant Tumors in the Liver Under Ultrasonic Imaging," [publication?] at p. 1663 (abstract) (May 1985).

Itoh, et al., "Angioscopic and Intravascular Ultrasound Imagings Before and After Percutaneous Holmium–YAG Laser Coronary Angioplasty," *American Heart Journal*, vol. 125, pp. 556–558 (Feb. 1993).

Jolesz, et al., "MR Imaging of Laser–Tissue Interactions," *Radiology*, vol. 168, pp. 249–253 (1988).

LeCarpentier, et al., "Continuous Wave–Laser Ablation of Tissue: Analysis of Thermal and Mechanical Events," *IEEE Tranactions on Biomedical Engineering*, vol. 40, pp. 188–200 (Feb. 1993).

Malone, et al., "Sonographic Changes During Hepatic Interstitial Laser Photocoagulation: An Investigation of Three Optical Fiber Tips," *Investigative Radiology*, vol. 27, pp. 804–813 (Oct. 1992).

NolsNe et al., "Interstitial Hyperthermia of Colorectal Liver Metastases with a US–Guided Nd–YAG Laser with a Diffuser Tip: A Pilot Clinical Study," *Radiology*, vol. 187, pp. 333–337 (May 1993).

NolsNe et al., "Ultrasonically Guided Interstitial Nd–YAG Laser Diffuser Tip Hyperthermia: An In Vitro Study," *Scand. J. Urol. Nephrol. Suppl.*, vol. 137, pp. 119–124 (1991).

Parker, D., "Applications of NMR Imaging in Hyperthermia: An Evaluation of the Potential for Localized Tissue Heating and Noninvasive Temperature Monitoring," *IEEE Transactions on Biomedical Engineering*, vol. BME–31, pp. 161–167 (Jan. 1984).

Roth, R. and Aretz, H., "Transurethral Ultrasound–Guided Laser–Induced Prostatectomy (Tulip Procedure): A Canine Prostate Feasibility Study," *The Journal of Urology*, vol. 146, pp. 1128–1135 (Oct. 1991).

Steger, A.C., "Interstitial Laser Hyperthermia for the Treatment of Hepatic and Pancreatic Tumours," *Photochemistry and Photobiology*, vol. 53, pp. 837–844 (1991).

Steger, et al., "Ultrasound Features of Low Power Interstitial Laser Hyperthermia," *Clinical Radiology*, vol. 46, pp. 88–93 (1992).

Tracz et al., "Magnetic Resonance Imaging of Interstitial Laser Photocoagulation in Brain," *Lasers in Surgery and Medicine*, vol. 12, pp. 165–173 (1992).

Tracz, et al., "Comparison of Magnetic Resonance Images and the Histopathological Findings of Lesions Induced by Interstitial Laser Photocoagulation in the Brain," *Lasers in Surgery and Medicine*, vol. 13, pp. 45–54 (1993).

Van Hillegersberg, et al., "Water–Jet–Cooled Nd:YAG Laser Coagulation of Experimental Liver Metastases: Correlation Between Ultrasonography and Histology," *Lasers in Surgery and Medicine*, vol. 13, pp. 332–343 (1993).

Watanabe, et al., "Thermally Controlled Laser Irradiation of the Myocardium with Intraoperative Ultrasound Monitoring," *PACE*, vol. 13, pp. 653–662 (May 1990).

Wyman et al., "Medical Imaging Systems for Feedback Control for Interstitial Laser Photocoagulation," *Proceedings of the IEEE*, vol. 80, pp. 890–902 (Jun. 1992).

Yock, et al., "Intravascular Ultrasound as a Guiding Modality for Mechanical Atherectomy and Laser Ablation," *Echocardiography*, vol. 7, pp. 425–431 (1990).

Yock, et al., "Intravascular Ultrasound Imaging for Guidance of Atherectomy and Other Plaque Removal Techniques," *International Journal of Cardiac Imaging*, vol. 6, pp. 179–189 (1991).

Hashimoto, D., Takami, M., and Idezuki, Y., "In–Depth Radiation Therapy by YAG Laser for Malignant Tumors in the Liver Under Ultrasonic Imaging," *Ultrasound in Medicine & Biology*, Supp. 1, vol. 78, p. 1663 (abstract) (May 1985).

Amin, et al., "Technical Note: Interstitial Laser Photocoagulation for the Treatment of Prostatic Cancer," *Brit. J. Radiol.*, 66:1044–1047 (Nov. 1993).

Declaration of Dr. Jonathan Ophir, dated Jun. 2, 1995, with Exhibit A.

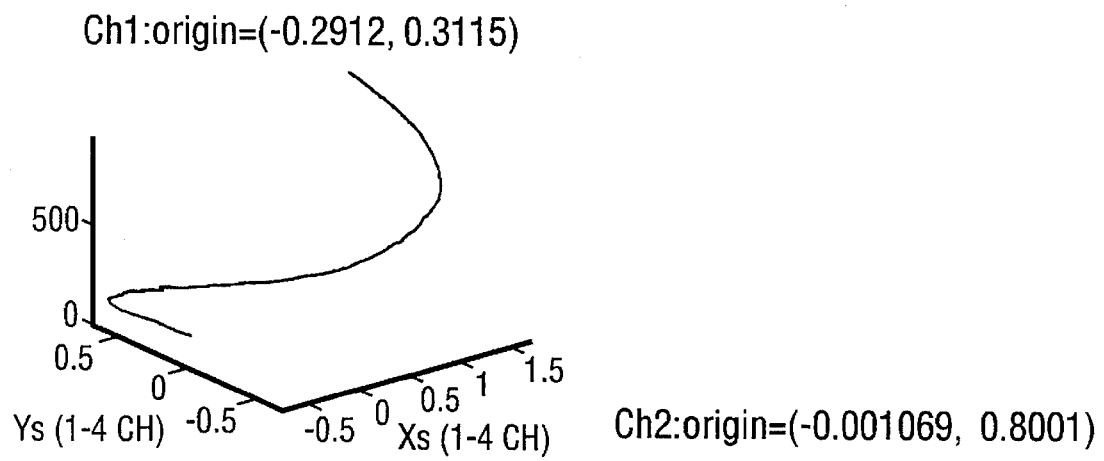
FIG. 12
FIG. 12a
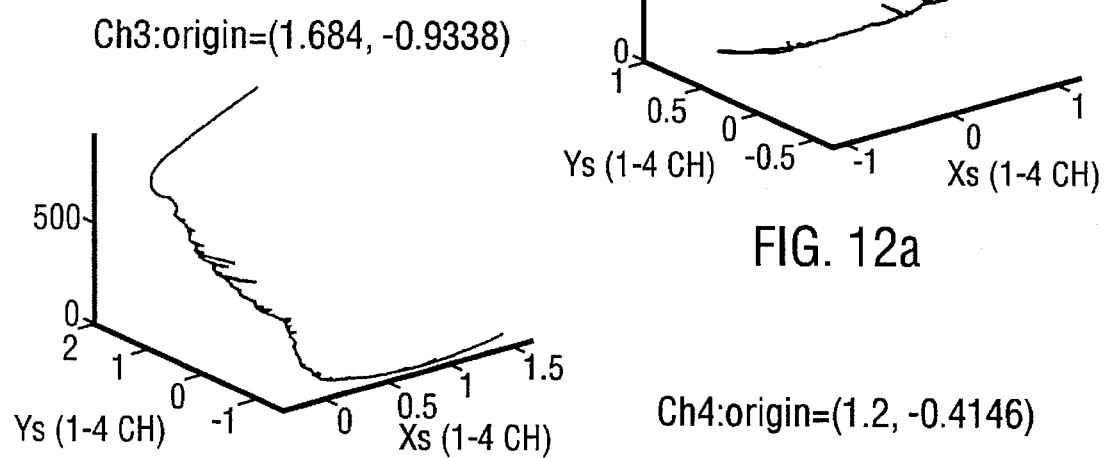
FIG. 12b
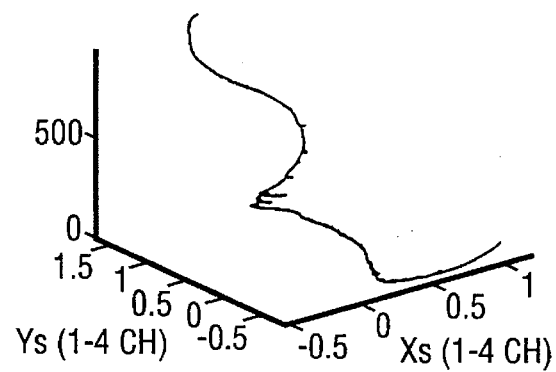
FIG. 12c

Ch1:origin=(-0.4906, 0.2387)

Ch2:origin=(-0.06565, -0.05914)

Ch3:origin=(0.1246, 0.1044)

Ch4:origin=(0.1164, 0.07197)

APPARATUS AND METHOD FOR NONINVASIVE DOPPLER ULTRASOUND-GUIDED REAL-TIME CONTROL OF TISSUE DAMAGE IN THERMAL THERAPY

This application is a continuation of application Ser. No. 08/446,199, filed May 19, 1995, now abandoned, which is a continuation of application Ser. No. 08/237,348, filed May 3, 1994, now abandoned.

The U.S. Government owns rights in the present invention pursuant to a grant No. HL22512 from the National Institutes of Health.

BACKGROUND OF THE INVENTION

The present invention relates to non-invasive, real-time Doppler ultrasonic monitoring and feedback control of the extent and geometry of thermal damage in tissue treated by thermal therapy.

In recent years, thermal therapy using various modalities to thermally destroy benign and malignant lesions like tumors has gained widespread acceptance. The thermal modalities include lasers, electromagnetic wave, thermistors, and ultrasound. Thermal energy is delivered to the tissue of interest either externally or by interstitial means.

Hyperthermia is a popular thermal therapy for tumors and other tissue-related diseases. According to this method of treatment, a tumorous region inside a patient's body cavity is warmed to and kept at a temperature range of about 42° to 50° C. A number of methods of inducing hyperthermia have been tried, including electromagnetic wave (radiofrequency and microwave), whole body heating by external and extracorporeal means, and ultrasound. Hyperthermia has been applied both externally and by interstitial methods. However, with all these techniques, the problem exists of getting the energy to the target to cause the required cell death with predictability and precision, yet causing little or no damage to surrounding tissues. This problem is particularly pronounced with the heating of deep seated tumors, such as those in the liver.

Because they can be accurately focused and controlled, lasers in particular have become an accepted tool for thermal treatment (e.g., hyperthermia, tissue coagulation and ablation). Lasers are especially suited for thermal therapy, as they can deliver high energy directly into the tissue being treated so as to minimize the effects on surrounding normal tissue areas. The laser energy is typically applied to the tissue of interest through optical fibers. The optical fibers may be introduced percutaneously, via a blood vessel, through other body openings, or during surgical exposure of the tissue.

In addition to tissue heating and thermal injury, laser irradiation can lead to tissue vaporization, melting, ejection, and pyrolysis, which all result in removal of biological material. These effects have been collectively described as "tissue ablation," a process consisting of a cascade of events, each involving threshold dependent mechanisms. Tissue ablation can also result in charring and tearing of tissue.

In many thermal therapy procedures, the desire is to coagulate and kill the tissue rather than to ablate or vaporize it. In coagulation, the absorbed laser energy heats cells throughout the target volume to temperatures exceeding protein denaturation thresholds of approximately 65° C. The resulting protein denaturation induces coagulative necrosis.

Interstitial laser photocoagulation (ILP) is a technique by which sufficient laser energy is deposited at low power levels so that thermal diffusion causes tissue coagulation while avoiding significant tissue vaporization near the fiber tips. Coagulative necrosis is believed to occur immediately during interstitial laser treatment.

Accurately predicting tissue thermal damage according to theories and computer modelling is very difficult, if not impossible, and is also unreliable. This is due to the heterogeneity of tissues with respect to: (1) physical properties (e.g., optical and thermal properties); (2) tissue geometry; and (3) blood perfusion in tissues. The transport of thermal energy in tissues is a complex process involving conduction, convection, radiation, metabolism, evaporation and phase change. Additionally, the broad parameter space of treatment operation (energy delivered, operation duration and delivery geometry, etc.) dramatically influence the overall tissue response. All these factors result in nonuniformly distributed and highly dynamic temperature fields in tissues during thermal treatment, yielding highly unpredictable tissue thermal damage.

Thus, one of the major obstacles to effective and widespread applications of thermal therapies has been the lack of a reliable noninvasive and real-time detection method to determine the extent and geometry of tissue damage. Such techniques can not only improve the optimization of the treatment parameters, but can also provide means for protecting critical organs surrounding treated tissues, resulting in optimal treatment.

Although laser-induced damage extends deeply into the tissue, the visible effect to the naked eye is superficial. Therefore, the use of medical imaging apparatus has proved useful to evaluate tissue response during thermal therapy. Indeed, imaging laser-induced damage is currently a major challenge in the field of laser medicine. The imaging modalities presently available for the acquisition of clinical images include two-dimensional X-ray imaging, computed tomographic imaging (CT), magnetic resonance imaging (MRI), ultrasonography, two-dimensional radioisotope imaging, single photon emission computed tomography, positron emission tomography, thermography, and transillumination. Several of these methods have been proposed for measuring temperature and detecting tissue response during laser therapy, including implanted thermistors or thermocouples, CT imaging, MRI, and ultrasonic imaging.

Methods such as thermocouple or light-detector insertion can provide information about the light distribution or heat development at different points in the tissue. These parameters may be used as feedback tools for laser adjustment during therapy to achieve optimal localized tumor destruction. However, the effectiveness of such probes is limited because the probes have to be placed invasively into the tissue, and their position is rather critical.

The use of magnetic resonance imaging (MRI) has also been investigated as a means of visualizing tissue response during laser treatment. However, currently available MRI devices require a relatively long time to collect data for an image, and thus may not be used practically for real-time evaluation. MRI devices are also large and expensive.

Ultrasound imaging is another technique that has gained favor of late for use in conjunction with thermal therapy. In medical ultrasound imaging, pulses of longitudinal sound waves at frequencies from 1–20 MHz are emitted by one or more piezoelectric transducers into the body volume being imaged. Inside the body, ultrasound is attenuated through scattering (including reflection, refraction and diffraction) and absorption. The intensities and arrival times of ultrasound echoes, that is, of waves reflected back to the transducer(s) by internal acoustic boundaries, are measured and converted into images of the reflecting boundaries. For sound waves, a boundary is a spatial discontinuity in the acoustic impedance, defined in any medium as the product of the speed of sound and density. The speed of sound and acoustic impedance are temperature dependent.

Several investigators have reported expanding hyperechoic regions in ultrasonic images made during laser irradiation of tissues. For example, hyperechoic regions have been reported in pig liver during and after laser irradiation. See Malone, et al., "Sonographic Changes During Hepatic Interstitial Laser Photocoagulation: An Investigation of Three Optical Fiber Tips," *Investigative Radiology*, vol. 27, pp. 804–13 (Oct. 1992); Dachman et al., "US-Guided Percutaneous Laser Ablation of Laser Tissue in a Chronic Pig Model," *Radiology*, vol. 176, pp. 129–33 (1990). In some cases, it was reported that a growing hyperechoic region was found during irradiation which sometimes became hypoechoic after one hour. See Godlewski, et al., "Ultrasonic and Histopathological Correlations of Deep Focal Hepatic Lesions Induced by Stereotaxic Nd-YAG Laser Applications," *Ultrasound in Med. & Biol.*, vol. 14, pp. 287–91 (1988); Godlewski, et al., "Deep Localized Neodymium (Nd)-YAG Laser Photocoagulation in Liver Using a New Water Cooled and Echoguided Handpiece," *Lasers in Surgery and Medicine*, vol. 8, pp. 501–09 (1988). Hypoechoic regions have also been found in rat liver after laser treatment of tumors. Van Hillegersberg, et al., "Water-Jet-Cooled Nd:YAG Laser Coagulation of Experimental Liver Metastases: Correlation Between Ultrasonography and Histology," *Lasers in Surgery and Medicine*, vol. 13, pp. 332–43 (1993). Similarly, hypoechoic regions have been found in canine myocardium irradiated with a low power laser. Watanabe, et at., "Thermally Controlled Laser Irradiation of the Myocardium with Intraoperative Ultrasound Monitoring," *PACE*, vol. 13, pp. 653–62 (May 1990).

Because of the large increase in echogenicity which subsequently decreases when the laser is turned off, it has been postulated that vapor or microbubble formation is responsible for the increase. Residual echogenicity is probably related to changes in the structure and to reorganization of tissue during coagulation and ablation.

Air pockets created during interstitial laser photocoagulation, either as small bubbles or a cavity at the fiber tip, will generate strong ultrasound echoes. It is thus possible to obtain ultrasound contrast images of thermal lesions induced by thermal therapy. Further, the use of imaging systems for potential control of interstitial laser photocoagulation was recently reviewed, with mixed results. See Wyman et al., "Medical Imaging Systems for Feedback Control for Interstitial Laser Photocoagulation," *Proceedings of the IEEE*, vol. 80, p. 890–902 (June 1992). Both MRI and ultrasound were able to detect changes in tissue properties during and after laser irradiation. The results with ultrasound, however, were inconsistent. It was postulated that actual tissue vaporization (ablation) may be required to visually observe substantial and consistent increases in echogenicity. In addition, it appears that respiratory motion poses a problem for ultrasound image-based control of interstitial laser therapy.

In addition to enabling visual evaluation of the extent of thermal tissue damage, ultrasound has also been used to guide placement of a laser. See Roth, R. and Aretz, H., "Transurethral Ultrasound-Guided Laser-Induced Prostatectomy (Tulip Procedure): A Canine Prostate Feasibility Study," *The Journal of Urology*, vol. 146, pp. 1128–35 (Oct. 1991). Therein, a combined ultrasound/laser device is described for transurethral laser coagulation of the prostate. Ultrasonic images were used for guidance and also for evaluating the results of laser treatment in dogs. At higher laser power levels (i.e., greater than 50 watts), hyperechoic regions correlating to the area of coagulation necrosis were seen.

Laser ablation of atherosclerotic plaques is another area where real-time monitoring is needed. See Borst, et al., "Laser Ablation and the Need for Intra-Arterial Imaging," *International Journal of Cardiac Imaging*, vol. 4, pp. 127–33 (1989). Several investigators have used ultrasound guidance for laser ablation of plaques with mixed results. For example, in Aretz, et al., "Intraluminal Guidance of Transverse Laser Coronary Atherectomy," *International Journal of Cardiac Imaging*, vol. 4, pp. 153–57 (1989), the concept of a combined laser and atherectomy and ultrasonic imaging catheter is described. This device was subsequently evaluated for imaging (but not lasing) in dogs. Aretz, et al., "Ultrasound Guidance of Laser Atherectomy," *International Journal of Cardiac Imaging*, vol. 6, pp. 231–37 (1991). Also, in Duda et al., "Ultrasound-Monitored Laser Angioplasty: Preliminary Clinical Results," *Cardiovasc. Intervent. Radiol.*, vol. 16, pp. 89–92 (1993), a clinical use of a combined laser angioplasty and ultrasonic imaging catheter to treat femoral and iliac stenoses was reported. The ultrasound image was found not to be useful in directing laser ablation, but it was found useful to measure the residual stenosis after treatment. Cavitation bubbles were seen in the blood during irradiation, but no changes in the echogenicity of the vessel wall were noticed after laser treatment. A major problem reported was that the ultrasound beam scanned radially while the laser beam was axial to the catheter, thereby preventing real-time monitoring.

An ultrasonic displacement measuring system based on Doppler ultrasound principles has been described for detecting myocardial thickening. See Hartley, et al., "An Ultrasonic Method for Measuring Tissue Displacement: Technical Details and Validation for Measuring Myocardial Thickening," *IEEE Transactions on Biomedical Engineering*, vol. 38, pp. 735–747 (Aug. 1991), the disclosure of which is herein incorporated by reference.

The technique is based on principles of both pulse-echo and pulsed Doppler ultrasound. By detecting and following the phase of the echoes returned from the transducer, the motion of the reflector with respect to the transducer can be quantified. The instantaneous phase of the returning echo is proportional to the distance of the reflector from the transducer. See Hartley et al. (1991) at p. 736. Using a tone burst mode of operation, the transmitted signal ($S_t$) has the following form:

$$S_t = \cos(\omega t), \quad \text{for } nT < t < nT + t_x \qquad (1)$$
$$= 0 \quad \text{elsewhere}$$

where $\omega$ is the angular frequency of the transmitted wave, T is the pulse repetition period which must be an integer number of cycles of $\omega$, n is a positive integer, and $t_x$ is the duration of the transmitted burst. This tone burst is propagated from the transducer toward a target where part of it is reflected back toward the transducer which then acts as a receiver.

The received echo signal ($S_r$) has the form $$S_r = a\cos\{\omega(t-t_d)\} \quad (2)$$

$$\text{for } nT+t_d < t < nT+t_d+t_x$$

$$= 0 \quad \text{elsewhere}$$

where a is the amplitude of the received echo signal and $t_d$ is the time delay between the beginning of the transmitted burst and the beginning of the received echo signal. In turn, $$t_d = 2d/c \quad (3)$$

where d is the distance from the transducer to the reflecting interface and c is the speed of sound in the target. Rearranging and substituting results in:

$$S_r = a\cos(\omega t - 2\omega d/c), \text{ for } t \text{ as in eq. (2)}. \quad (4)$$

Since $\omega=2\pi c/\lambda$, eq. (4) can be put in the form $$S_r = a\cos(\omega t - \phi), \text{ for } t \text{ as in eq. (2)}, \quad (5)$$

where $\lambda$ is the wavelength of the ultrasonic wave in the conducting medium (such as tissue), and where $$\phi = 4\pi d/\lambda. \quad (6)$$

In eq. (6), $\phi$ represents the phase (in radians) of the echo signal with respect to the transmitter signal and is directly proportional to the distance d from the transducer to the reflecting target.

A block diagram of a prior art ultrasonic displacement measuring instrument is shown in FIG. 1. In the instrument described in FIG. 1, phase is sensed by a quadrature-phase detector 32 consisting of two analog multipliers. The reference inputs to the multipliers are cos ($\omega t$) [27] and sin ($\omega t$) [29] and are derived from a master oscillator 26 which runs continuously at angular frequency $\omega$. Multiplying each of these signals by the echo signal results in $$\cos(\omega t) \times a\cos(\omega t-\phi) = a\{\cos(2\omega t-\phi)+\cos(\phi)\}/2 \quad (7)$$

and $$\sin(\omega t) \times a\cos(\omega t-\phi) = a\{\sin(2\omega t-\phi)+\sin(\phi)\}/2 \quad (8)$$

for t as in eq. (2).

If the above signals are low-pass filtered to remove the high frequency terms at $2\omega t$, are multiplied by 2 to eliminate the ½, and are sampled only during the received interval [i.e., t as in eq. (2)], the sampled, phase detected signals then become $$x = a\cos\phi \quad (9)$$

and $$y = a\sin\phi, \quad (10)$$

where x and y can be considered as components of a polar coordinate phase vector of length a and angle $\phi$. Components x and y are called "quadrature range-phase signals."

In general, the target will be moving with respect to the transducer, which will generate a Doppler shift and cause a rotation of the phase vector. To see how the phase and Doppler shift frequency are related, consider a target moving at velocity v at an angle $\theta$ with respect to the sound beam axis. Its distance from the transducer d is given by $$d = \int_0^t v\cos\theta \, dt = vt\cos\theta + d_0 \quad (11)$$

where $d_0$ is the initial position of the target. If eq. (11) is substituted into eq. (6), phase also becomes a function of time given by $$\phi = (4\pi vt/\lambda)\cos\theta + \text{constant}. \quad (12)$$

Differentiating the phase yields an angular frequency ($\omega_d$):

$$\omega_d = d\phi/dt = (4\pi v/\lambda)\cos\theta. \quad (13)$$

Substituting $\omega_d = 2\pi f_d$ and $\lambda = c/f$, eq. (13) becomes $$f_d = (2fV/c)\cos\theta, \quad (14)$$

which is the well-known Doppler equation with $f_d$ being the Doppler shift frequency, in Hz, of the reflected wave. The Doppler shift can thus be obtained from the phase by differentiation. For a moving target, the phase vector rotates with an angular frequency given by $\omega_d$ in a direction corresponding to the direction of the target motion: clockwise for motion away from the transducer (receding phase) or counterclockwise for motion toward the transducer (advancing phase).

Timing for the instrument shown in FIG. 1 (operated at 10 MHz) is controlled by 10 MHz crystal oscillator 26. The 10 MHz frequency is divided by 2560 by frequency divider 14 to produce a pulse repetition frequency (PRF) of 3.90625 kHz. A 0.4 μs pulse from pulse generator 12 is used to gate 4 cycle bursts of the 10 MHz signal [see eq. (1)] to transmitter amplifier 28, which drives ultrasonic transducer 10. Transducer 10 converts the electrical signals to acoustic tone bursts, which are propagated into the tissue where they are reflected by structures along the sound beam. The echoes returning to transducer 10 are converted back into electrical signals [see eq. (2)], which are amplified by RF amplifier 30 to produce signal 31 (see eq. (4)) and compared by quadrature-phase detector 32 in phase to quadrature signals {cos ($\omega t$) [27] and sin ($\omega t$) [29]} from 10 MHz oscillator 26. The two phase detector outputs 33 and 35 (which are quadrature signals that correspond to eq. (7) and (8), respectively) are then sampled by dual sample and hold circuit 34 with a 0.2 μs range-gate pulse 24 delayed by 2–50 μs from the transmit pulse by variable delay circuit 18. The range of circuit 24 is selected by potentiometer 16. After sampling, the two signals are high-pass filtered at 1 Hz to remove the dc components from the stationary structures and low-pass filtered at 1 kHz by dual filters 36 to remove residual signals. Except for the lower bandwidth, the sampled, filtered signals 37 and 39 are the in-phase (I) and quadrature-phase (Q) Doppler signals (which correspond to eq. (9) and (10), respectively). Signals 37 and 39 resemble quadrature audio signals from a pulsed Doppler instrument for measuring blood flow, and may be received at output 52.

The vector representation of the quadrature signals may be shown in X–Y display 54 shown in FIG. 1. The radius a represents the amplitude of the echo from the target, and the phase $\phi$ of the echo represents the position of the target. The change in position (or displacement) can be measured by noting the direction (clockwise or counterclockwise) and counting the revolutions of the vector. Each revolution corresponds to reflector motion of 0.075 mm at 10 MHz. To improve the resolution of the instrument to 0.019 mm, revolutions are counted in 90° increments corresponding to axis crossings in the X–Y display 54. Logic circuits in up-down counter controller 40 detect positive and negative zero crossings of each quadrature signal, assign a direction based on the polarity of the zero crossing and the polarity of the other signal at the time, and increment or decrement 8-bit up-down counter 40. Full-scale range for the 8-bit counter shown is about 4.8 mm. Digital-to-analog converter (DAC) 44 receives 8-bit output 42 from counter 40 and produces a voltage output 46 that represents the change in position of echoes within the sample volume with a calibration of 2 V/mm. Since no filter is used on displacement output 46, it is updated after each sample (approximately 4 kHz) whenever the reflector has moved 0.019 mm.

Signals available from the instrument shown in FIG. 1 include: displacement 46 at 2 V/mm, analog range 20 at 0.1 V/cm, quadrature signals 52, and quadrature audio 52a from audio amplifier 50 and speaker 48. In addition, monitor outputs 21, 25, and 33 for oscilloscope 22 are provided from transmit pulse generator 12 (for triggering), range-gate pulse generator 24, and phase detector 32, respectively. Controls are a 2–40 mm range-gate potentiometer 16 and a 6, 7, or 8 bit limit switch 41 to up/down counter 40. Inputs are from a 10 MHz piezoelectric transducer 10 attached or planted within the tissue of interest, and a reset command 55 from a triggered event.

No provision is made in the prior art circuit of FIG. 1, however, for real-time evaluation of the signals received by transducer 10 in relation to tissue thermal response, nor of controlling the extent or geometry of tissue thermal damage resulting from thermal treatment of a lesion in living tissue. Thus, a need exists for an apparatus and method for noninvasive, real-time monitoring and control of the extent and geometry of tissue damage in thermal therapies.

SUMMARY OF THE INVENTION

The problems outlined above are addressed by the apparatus and method of the present invention. That is, the purposes of the present invention are: (1) to provide a noninvasive, reliable and inexpensive technique that can monitor in real time the extent and geometry of thermal damage and temperature profile in tissues induced by various forms of thermal therapy; and (2) to utilize the signal provided by such a technique as a feedback signal to automatically or manually regulate modulation parameters of various thermal modalities, thereby controlling thermal output in various thermal treatment procedures.

The present invention broadly comprises a single-beam Doppler ultrasound configuration based on the principles described above. In one embodiment, a laser fiber optic is incorporated into an ultrasound transducer with the sound and laser beams collinear. In another preferred embodiment, the transducer is separate from the thermal modality, which may be a laser, a thermistor, or other thermal treatment instrument. Unlike previously described non-Doppler ultrasound configurations, which produce only a two-dimensional visual image of the treatment site for visual inspection, this ultrasonic Doppler configuration may be operated in A-mode, M-mode, or multi-dimensional image mode to allow measurement of echogenicity and motion in tissue along the sound beam produced by the transducer. Furthermore, the present invention uses the ultrasonic Doppler signals to automatically regulate modulation parameters (such as pulse rate, exposure time and output power of a laser or other thermal modality) so that desired thermal treatment can be achieved without damaging critical organs surrounding treated tissues. The Doppler signals can also be displayed on a monitor to allow manual feedback control of the treatment parameters by a human operator.

The method for ultrasonic Doppler detection of tissue response to thermal therapy according to the present invention broadly comprises providing an echo-Doppler transmitter/receiver coupled to a transducer, emitting ultrasonic waves from the transducer toward the region of a tissue receiving thermal therapy, receiving echoes from the thermally treated tissue, and converting the echoes to electrical echo signals, where the echo signals each contain a phase vector. The x and y components of the phase vector of each echo signal are derived as functions of range and time. The x and y components are sampled to produce multiple pairs of I and Q Doppler signals indicating motion and echogenicity of the tissue relative to the transducer at a plurality of tissue depths. The I and Q Doppler signals are then evaluated to determine the spatial profile of tissue temperature and the extent and geometry of tissue damage resulting from said thermal therapy. The evaluation results may be displayed for visual inspection and evaluation.

Evaluation of the Doppler signals comprises eliminating background signals in I and Q Doppler signals to produce background-motion-free I and Q Doppler signals and processing the background-motion-free I and Q Doppler signals to produce current dominant shift Doppler frequencies and accumulated dominant Doppler frequencies. The current dominant shift Doppler frequencies and accumulated dominant Doppler frequencies are then used to produce tissue temperature reading at multiple tissue depths and a reading indicating the extent and geometry of tissue thermal damage. A current tissue irreversible damage front is then determined from the tissue temperature reading and from the extent and geometry of tissue thermal damage and is compared to a user-desired tissue irreversible damage front to produce a modulation signal for regulating the modulation parameters, thus controlling thermal output of the thermal modality.

An apparatus for ultrasonic Doppler monitoring of the extent and geometry of tissue damage resulting from thermal therapy according to the present invention comprises an echo-Doppler transmitter/receiver for emitting ultrasonic waves toward the region of a tissue receiving thermal therapy, for receiving echoes from the treated tissue, and for converting the echoes to electrical signals, where the electrical signals each contain a phase vector. The echo-Doppler transmitter/receiver is coupled to an echo-signal processing means for deriving x and y components of the phase vector of each echo signal as functions of range and time and for outputting multiple pairs of I and Q Doppler signals, indicating echogenicity and motion in the tissue relative to the transducer at a plurality of tissue depths. The I and Q Doppler signals are also evaluated by several modules for determining tissue temperature at multiple tissue depths and for determining the geometry and the extent of tissue damage resulting from said thermal therapy. The evaluation results may be displayed on a variety of devices, including a color monitor.

The echo-signal processing means comprises, for example, a quadrature-phase detector coupled to the echo-Doppler transmitter/receiver for outputting x and y Doppler signals, a delayed pulse generator coupled to the echo-Doppler transmitter/receiver for producing range-gate pulses, a dual sample/hold circuit coupled to the quadrature-phase detector and the pulse generator for receiving x and y Doppler signals and range-gate pulses and for producing multiple pairs of I and Q Doppler signals, and a lowpass filter coupled to receive the I and Q Doppler signals from the dual sample/hold circuit.

The evaluating means comprises, for example, a circuit coupled to the Doppler detector for receiving pairs of I and Q Doppler signals and for eliminating background noise in the I and Q Doppler signals to produce background-motion-free I and Q Doppler signals. The background-motion-free I and Q Doppler signals are then processed by circuitry to produce current dominant shift Doppler frequencies and accumulated dominant Doppler frequencies. Fuzzy logic circuitry utilizes the current dominant shift Doppler frequencies and accumulated dominant Doppler frequencies to produce tissue temperature readings at multiple tissue depths and readings indicating the extent and geometry of tissue thermal damage. The fuzzy logic circuitry also determines a tissue irreversible damage front from the tissue temperature and tissue thermal damage readings. Finally, another fuzzy logic circuitry is used to compare the current tissue irreversible damage front to a user-desired tissue irreversible damage front to produce a modulation signal for regulating the modulation parameters of the thermal modality to achieve controlled thermal output. Manual feedback control of thermal modalities can also be achieved according to the displayed Doppler ultrasound signals.

The present invention can be widely used to monitor temporal and spatial progress of thermal damage and tissue temperature during thermal therapies, and thus is useful for hyperthermia, thermal coagulation and ablation treatments.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and can be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

FIGS. 9 to 9g correspond to range gates 1 to 8, respectively.

FIGS. 10 to 10g correspond to range gates 1 to 8, respectively.

FIGS. 12 to 12g correspond to range gates 1 to 8, respectively.

FIGS. 13 to 13g correspond to range gates 1 to 8, respectively.

FIG. 14 illustrates a block diagram of the experimental setup for detecting thermal response in the fresh canine liver sample being irradiated by a laser using the ultrasound system of FIG. 2a.

FIGS. 15 to 15g correspond to range gates 1 to 8, respectively.

EXPERIMENTAL RESULTS

The structure and operation of apparatus according to the present invention can be appreciated by reference to the following experimental results.

1. Experimental Results Using a Single-Range-Gate Pulsed Doppler Detector

Figure 1:
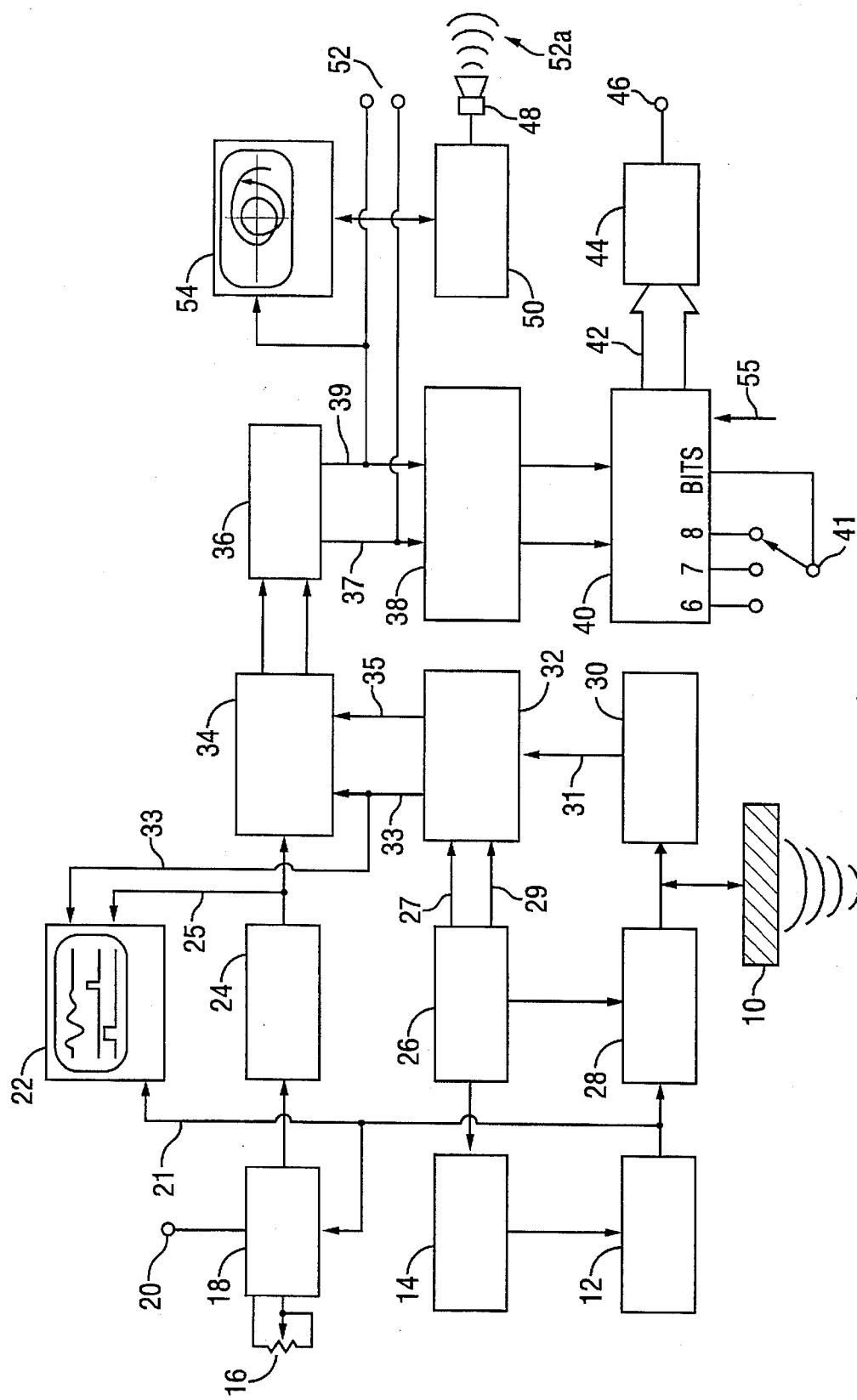
FIG. 1 is a block diagram of a prior an single-range-gate ultrasonic Doppler displacement measurement system operating at 10 MHz.
Figure 2:
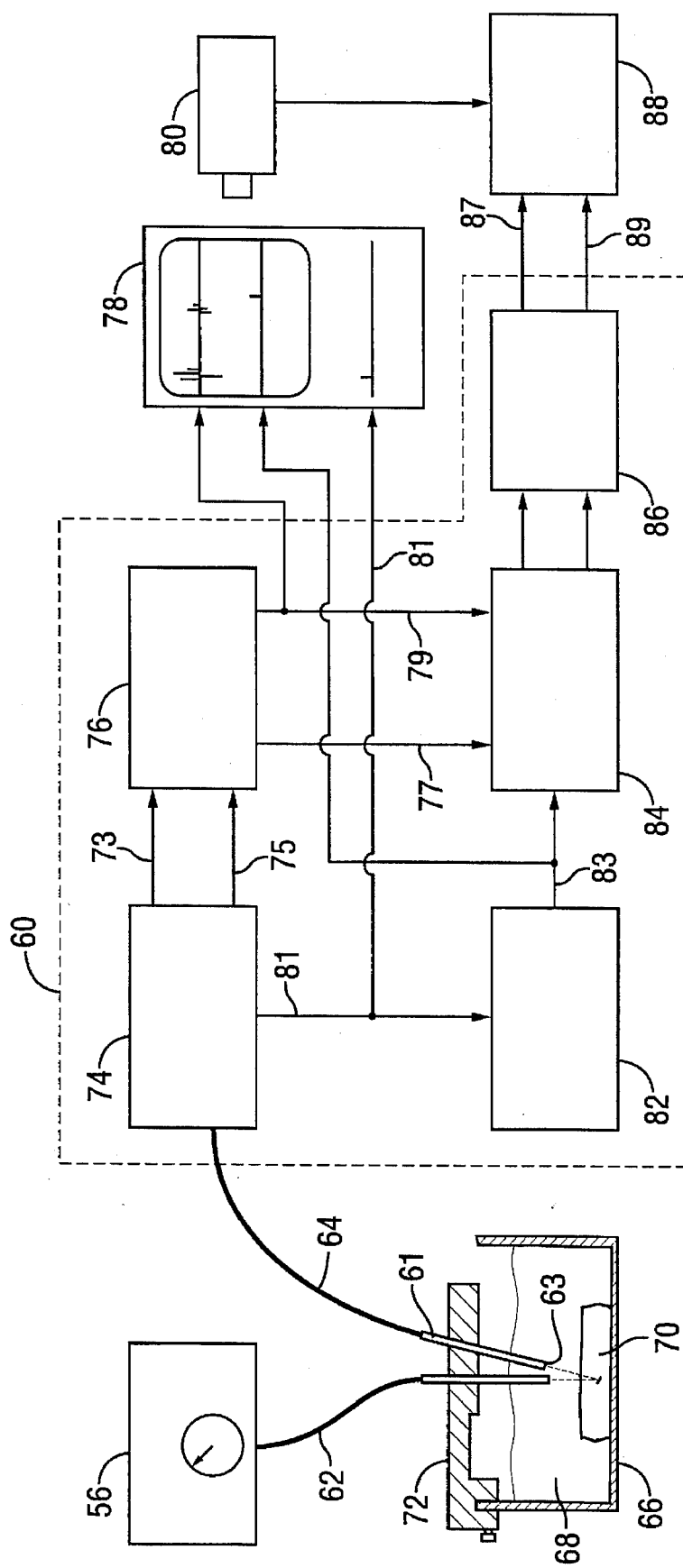
FIG. 2 is a block diagram of an experimental set-up of a single-range-gate pulsed Doppler detector for detecting laser-tissue interaction according to the present invention.

Pulsed Doppler detector 60 shown in FIG. 2 comprises 1 mm ultrasound transducer 64 coupled to 20 MHz Doppler transmitter/receiver 74, which was used experimentally to analyze the amplitude and phase of echoes along the laser beam generated by laser 56 through optical fiber 62 before, during, and after laser irradiation of tissue 70 in-vitro. The 20 MHz Doppler transmitter/receiver 74 for sensing motion in tissue was based on the 10 MHz ultrasonic displacement measurement system shown in FIG. 1, as described in Hartley, et al. (1991) and supra. The components 38, 40 and 44 in FIG. 1 were not needed. The modifications made to convert the system of FIG. 1 from a 10 MHz system to a 20 MHz system will be apparent to those of skill in the art.

The studies were done in-vitro using fresh lean beef steak (muscle) and liver (tissue 70) submerged in water 68 in tank 66 using the apparatus as shown in FIG. 2. Fiber optic 62 (600μ in diameter) and ultrasound transducer 64 were fixed in holder 72 with their tips about 5 mm above the surface of the tissue 70 and angled at 8° so that the beams intersected slightly below the surface of the tissue 70. The beams were placed within about 1 mm of each other from the surface to a depth of 5 mm. Laser 56 (805 nm diode laser from Diomed, Cambridge, UK) was used to irradiate tissue 70 for approximately 30 to 180 seconds at calibrated power levels ranging from 4 to 23 watts (after compensating for fiber efficiency). The spot size or diameter of the laser beam at the surface of the tissue 70 was about 2 mm.

The Doppler transmitter/receiver 74 was connected to a 1 mm diameter piece of piezoelectric ceramic (PZT-5A) 63 mounted to the blunted tip of a 16 gauge needle 61. Eight cycle bursts of sound were transmitted into tissue 70 and the returning echoes 75 were processed by quadrature-phase detector 76, which is similar to that used in a pulsed Doppler velocimeter. Quadrature-phase detector also received 20 MHz signal 73 from Doppler transmitter/receiver 74. The outputs 77, 79 from quadrature-phase detector 76 were the x and y components of the phase vector as functions of range and time. The phase of the echo signal is $\tan^{-1}$ (y/x) and the amplitude is $(x^2+y^2)^{1/2}$. Both outputs thus contained amplitude and phase information, but are commonly referred to as quadrature range-phase signals. One of the phase detector outputs 79 was displayed on oscilloscope 78 along with a range-gate pulse 83 from pulse generator 82, which was used to sample the detected echoes after a variable time delay. Sync signal 81 from Doppler transmitter/receiver 74 was applied as the trigger input to oscilloscope 78.

The resulting outputs after sampling by dual sample hold circuit 84 were the in-phase (I) and quadrature-phase (Q) Doppler signals, which were low-pass filtered with a bandwidth from 0 to 5 kHz by bandpass filters 86. The Doppler outputs extend down to DC because no high-pass filter was used for our purpose, as is usually done in other Doppler applications (see FIG. 1). The oscilloscope display 78 of the range-phase signal 79 showed all the echoes along the sound beam while the Doppler I and Q signals allowed quantification and analysis of the echoes from a specific depth within the tissue.

For each exposure, a video image of the range-phase display and the I and Q Doppler signals (87, 89, respectively) was recorded from the selected depth on VCR 88 (Panasonic AG-7355). Using a time code generator (not shown), we also recorded the time from the beginning of each exposure. Following exposure, the tissue 70 was sliced open at the resulting lesion (if any) and photographed. The photographs were enlarged to 4 times actual size, and the lesions were analyzed for size and color. The presence and size of any charred, blackened, or dark areas were especially noted.

The video tapes were played back and the ultrasonic activity at each depth was characterized into one of three categories: type 0, no change in echo pattern from baseline; type 1, slow changes in phase with relatively constant amplitude; and type 2, large fluctuations in amplitude and phase which were usually random but occasionally showed some periodic structure. At each exposure we quantified the time and depth at which types 1 and 2 activity started, the maximum depth of each type of activity, the time to start of type 1 and 2 activity, and whether the type 2 activity showed periodicity. At the end of each exposure the change in echogenicity was estimated by measuring the maximum amplitude of the range-phase envelope divided by the maximum amplitude before exposure. The I and Q signals at the arbitrarily chosen depth were played back on X–Y oscilloscope 78 and also into a Doppler spectrum analyzer (SP25A Medasonics, Mt. View, Calif.) (not shown).

In general, two distinct types of activity were seen in the ultrasound displays during laser irradiation of the tissue. Type 1 activity was characterized by slow variations on the range-phase display and slowly rotating loops often changing in X–Y display of the I and Q signals. This activity is similar to what we see with tissue motion when measuring displacement with the device shown in FIG. 1. Type 2 activity was more chaotic with large amplitude fluctuations seen on the range-phase display and random motion on the X–Y display. Occasionally this motion became more periodic with rapid but small (<2π radians) oscillations in phase seen on the X–Y display. This activity is consistent with the appearance and disappearance or vibration of strong reflectors. Type 1 activity was primarily phase modulation with a Doppler frequency of less than 1 Hz while type 2 activity consisted of both amplitude and phase modulation with Doppler frequency components greater than 1 kHz and peak amplitudes more than 10 times greater than the previous type 1 levels.

Figure 3:
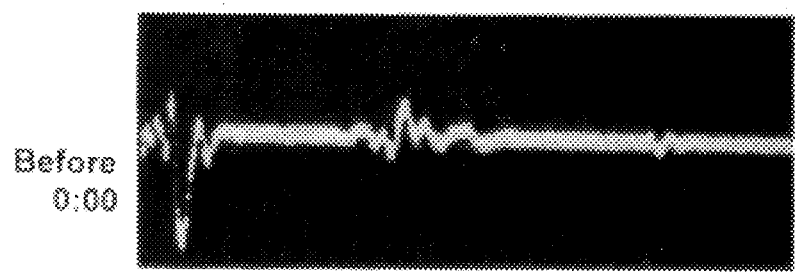
FIG. 3 is a range-phase display of echoes from beef liver before exposure to a diode laser using the experimental set up of FIG. 2.
Figure 3A:
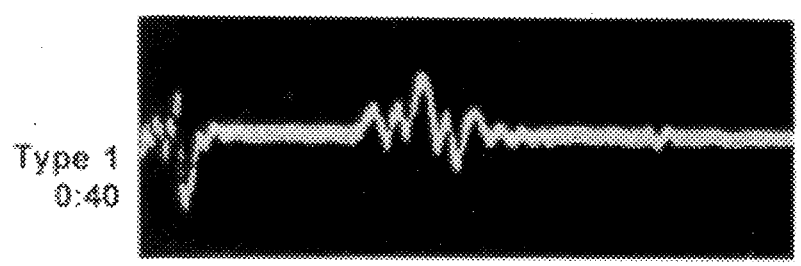
FIG. 3a is a range-phase display of echoes from beef liver after 40 seconds of exposure to a diode laser at 8 watts power using the experimental set up of FIG. 2.
Figure 3B:
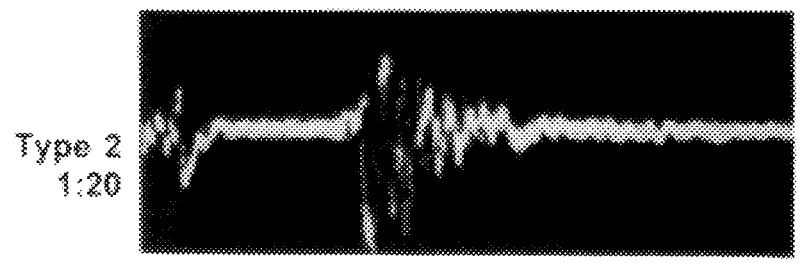
FIG. 3b is a range-phase display of echoes from beef liver after 80 seconds of exposure to a diode laser at 8 watts power using the experimental set up of FIG. 2.
Figure 3C:
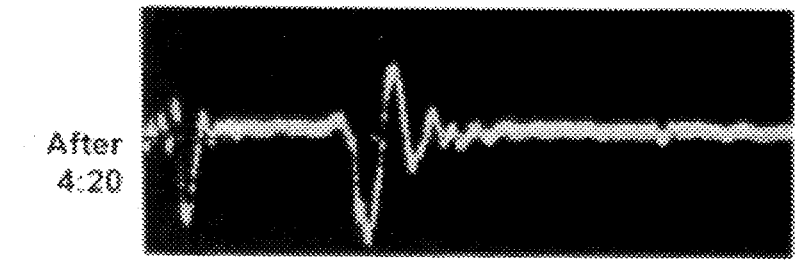
FIG. 3c is a range-phase display of echoes from beef liver after 260 seconds of exposure to a diode laser at 8 watts power using the experimental set up of FIG. 2.

The range-phase output of a typical exposure of beef liver is illustrated in FIGS. 3–3c. The x-axis represents tissue depth in mm, and the y-axis represents the y range-phase signal in volts. Before exposure, the tissue echogenicity was low, as shown in FIG. 3. Forty seconds after turning on the laser, the tissue activity was type 1 with slowly moving echoes of increasing echogenicity, as shown in FIG. 3a. At 80 seconds, the activity was type 2 with large random fluctuations in amplitude and/or phase extending 5 μs (3.8 mm) into the beef, as seen in FIG. 3b. As soon as the laser was turned off, the tissue activity reverted to type 1, as seen in FIG. 3c, with higher echogenicity than before exposure. Each photograph represents one video frame or approximately 1/30 second.

Figure 4:
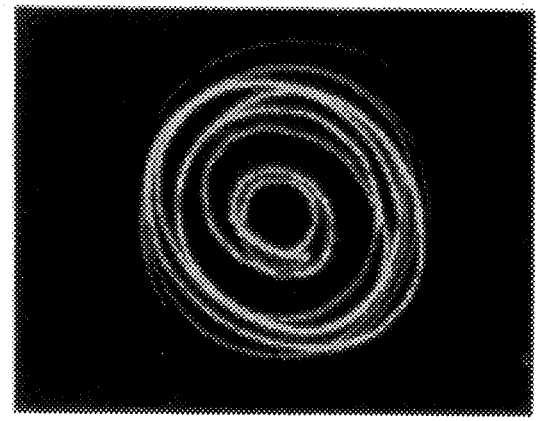
FIG. 4 is a Doppler vector display illustrating type 1 activity signals from tissue motion using the experimental set up of FIG. 2.
Figure 4A:
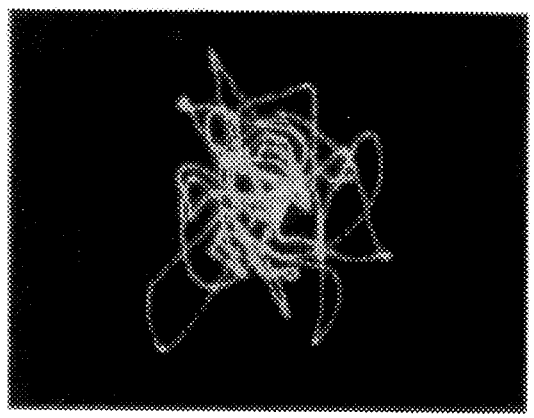
FIG. 4a is a Doppler vector display illustrating random type 2 activity signals from tissue motion using the experimental set up of FIG. 2.
Figure 4B:
FIG. 4b is a Doppler vector display illustrating periodic type 2 activity signals from tissue motion using the experimental set up of FIG. 2.

FIGS. 4–4b show an X–Y display of the I and Q Doppler signals during tissue motion and type 1 activity (FIG. 4), random type 2 activity (FIG. 4a), and periodic type 2 activity (FIG. 4b). This type of display shows the locus or motion of the Doppler vector during the time of the photograph. The amplitude is the distance from the center, and the phase is the angle to the X axis. The Doppler shift is the frequency of rotation with the direction of rotation (counterclockwise or clockwise) corresponding to the direction of tissue motion (toward or away from the transducer). Because the very slow motion of the tissues produces Doppler shifts of less than 1 Hz, the audio bandwidth of the VCR (20 Hz–30 kHz) does not allow recording of type 1 signals without distortion. It was also difficult to freeze a suitable X–Y display of type 1 activity in real-time during exposure. Therefore, the signal in FIG. 4 was made after exposure by moving the transducer with respect to the tissue while recording I and Q signals. Each revolution of the Doppler vector corresponds to tissue motion of 37.5 μm, and the frequency of rotation is the Doppler shift. This display is very similar to the slowly rotating X–Y displays seen during data acquisition with full bandwidth to DC. With zero or low level type 1 activity, the vector display from recorded data shows only a dot in the center of the display. With random type 2 activity, the Doppler vector shows random motion with no discernible loops as shown in FIG. 4a. During several of the exposures exhibiting random type 2 activity, we recorded transient narrow-band periodic activity as shown in FIG. 4b. The arcs are partial loops (≈70°) which would correspond to back and forth motion or vibration of a reflector of 0.1 wavelength or about 7 microns. Because of the 20 Hz AC coupling to the VCR, the centroid of the arcs is not in the center of the display.

Figure 5:
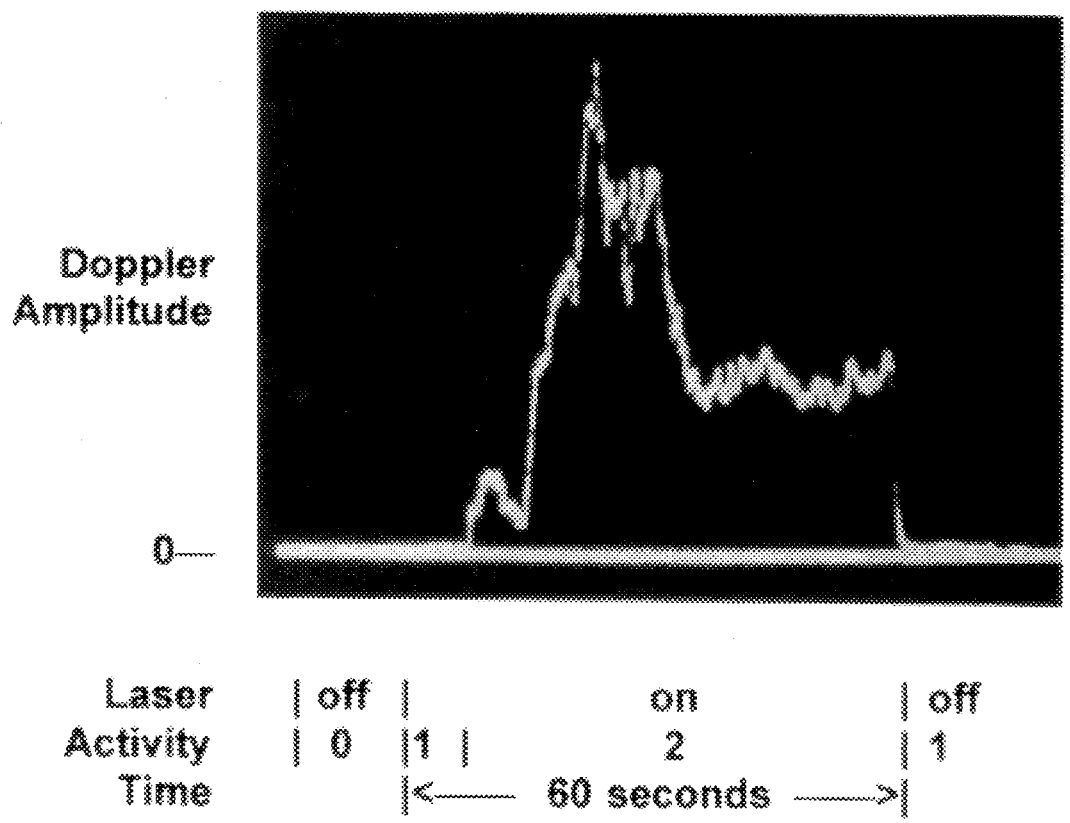
FIG. 5 is a plot of Doppler amplitude, versus time during one minute exposure of beef liver at 8 watts laser power using the experimental set up of FIG. 2.

To facilitate demonstration of the variation of the amplitude of the Doppler signal during an exposure, the I signal was played back through an amplitude detector consisting of a precision full-wave rectifier followed by a two-pole 2 Hz low-pass filter (not shown in FIG. 2). See Hartley, et al., "Doppler Quantification of Echo-Contrast Injections In Vivo," *Ultrasound in Med. & Biol.*, vol. 19, pp. 269–78 (1993), the disclosure of which is herein incorporated by reference. FIG. 5 shows the time course of the Doppler amplitude during a 60 second exposure to the diode laser at 8 watts power. Again, type 0 and type 1 activity show zero amplitude because of bandwidth limitations of the VCR while type 2 activity shows a high amplitude with much variability during the first half of the exposure. During the final 25 seconds the amplitude is fairly constant indicating steady state activity until the laser is turned off. The transition from type 1 to type 2 activity was usually a sudden event occurring 2 to 104 seconds after energizing the laser. After type 2 activity was initiated, it often increased or decreased in intensity and usually continued until the laser was turned off.

The data from all exposures are summarized in Table I. Of the 35 exposures analyzed, 28 showed visible lesions, which had blanched or light colored borders, and most had a visibly darker core. The dimensions of the lesions ranged from 3 to 6 mm in diameter with a core 1.5 to 3 mm diameter. The other 7 exposures showed no visible lesion. For simplicity, the lesions were characterized by the color of the core into 4 categories: black, dark, faint, and none. The transition from type 1 to type 2 activity (22 of 35 exposures) always started at the surface of the tissue and extended to an eventual depth of 1.5 to 4.5 mm (2 to 6 μs). Transient periodic or oscillatory activity was noted at the arbitrary sample volume depth in 10 of the exposures exhibiting type 2 activity. There was an increase in echo amplitude in 33 of the 35 exposures with an average increase of 5.5 fold. For those exposures showing only type 1 activity the increase was 1.9 versus 7.4 for the exposures showing type 2 activity.

Figure 6:
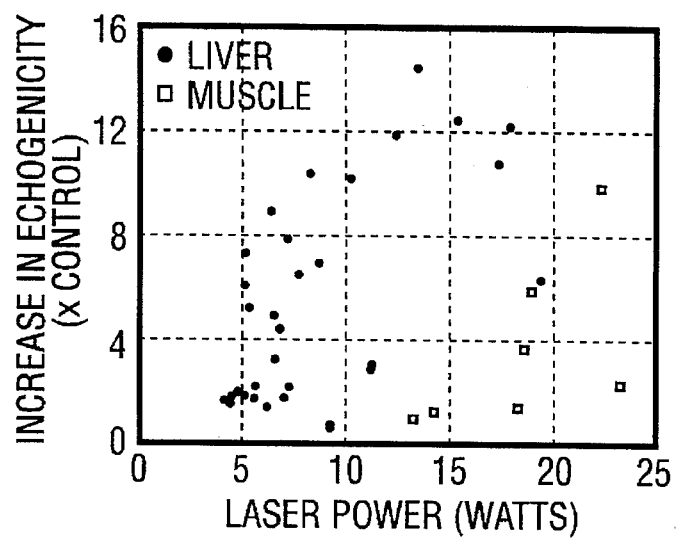
FIG. 6 is a plot of residual increase in echogenicity versus laser power for exposure of beef liver using the experimental set up of FIG. 2.
Figure 6A:
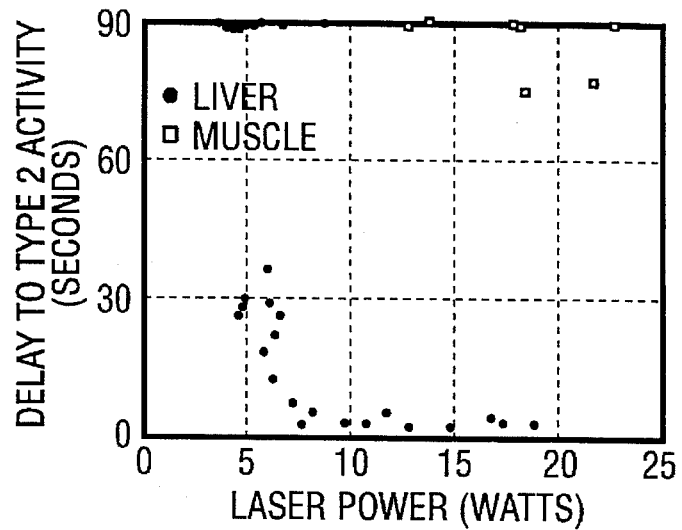
FIG. 6a is a plot of delay to the start of type 2 activity versus laser power for exposure of beef liver using the experimental set up of FIG. 2.
Figure 6B:
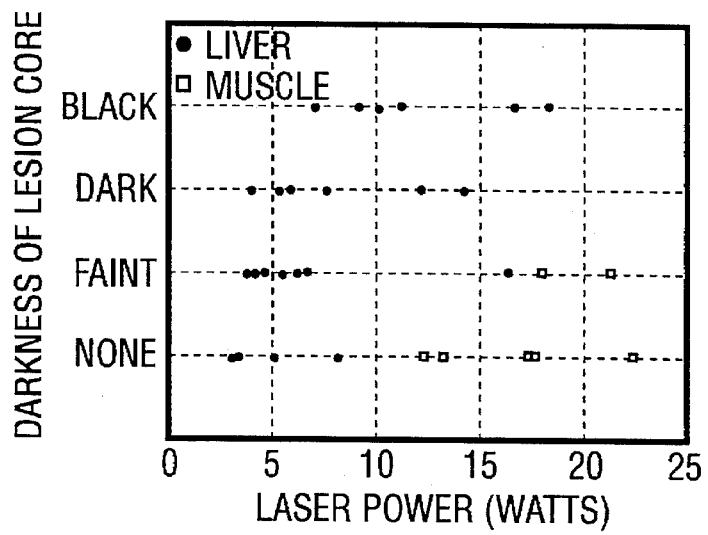
FIG. 6b is a plot of lesion severity versus laser power for exposure of beef liver using the experimental set up of FIG. 2.

FIGS. 6–6b show graphs of several of the measured parameters versus laser power for liver and muscle tissue. The residual echogenicity tends to increase with laser power for both liver and muscle, as shown in FIG. 6. The delay to the start of type 2 activity (if it occurred) shows a strong relationship to laser power for liver, but not for muscle in the range of power levels available, as shown in FIG. 6a. The darkness of the lesion core also shows a relationship to laser power for both liver and muscle, as shown in FIG. 6b. In these graphs, the data for liver and muscle are different with both tissue damage and ultrasonic changes occurring at lower power levels for liver than for muscle.

Figure 7:
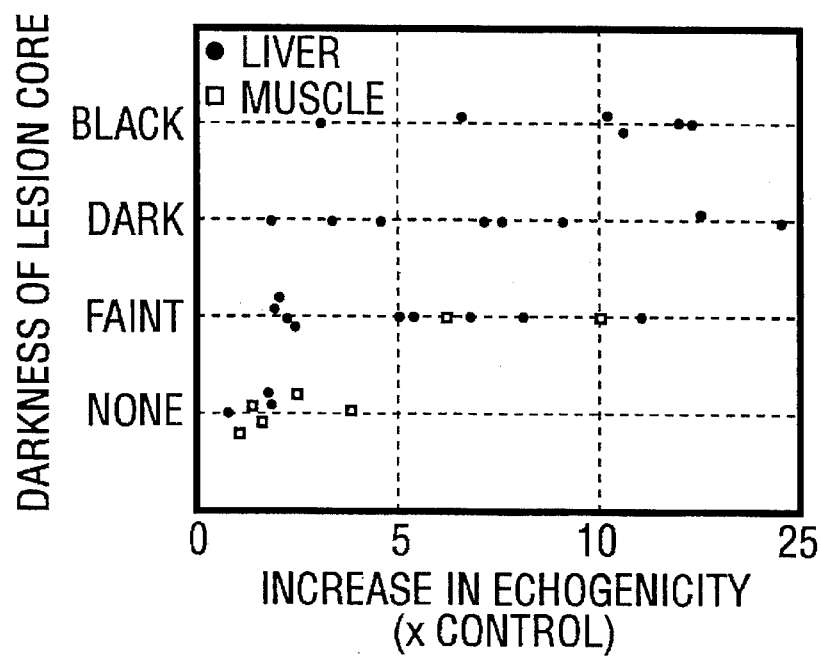
FIG. 7 is a plot of lesion severity versus residual increase in echogenicity for exposure of beef liver using the experimental set up of FIG. 2.
Figure 7A:
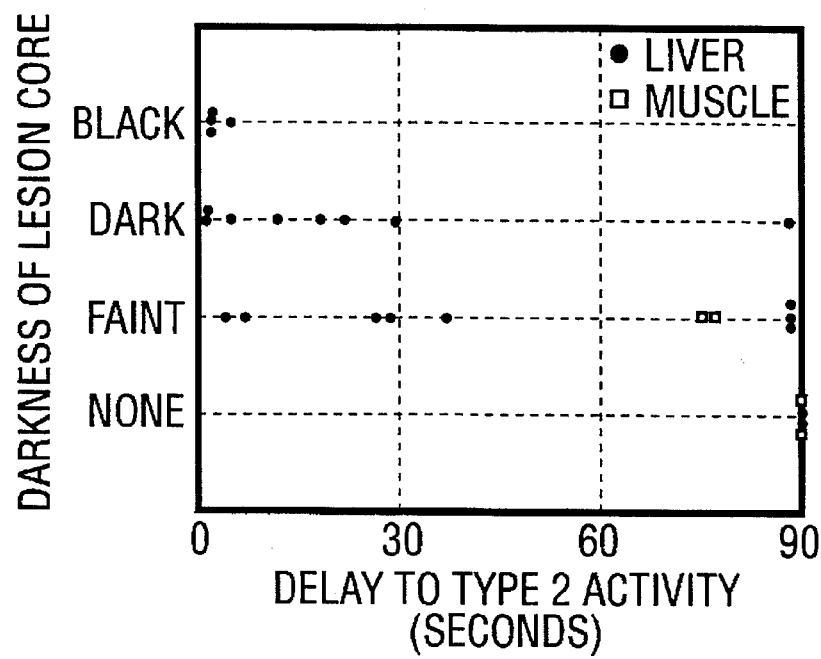
FIG. 7a is a plot of lesion severity versus delay to start of type 2 activity for exposure of beef liver using the experimental set up of FIG. 2.

FIGS. 7 and 7a show graphs of lesion severity (darkness of lesion core) versus ultrasonically derived parameters (increase in echogenicity in FIG. 7 and delay to the start of type 2 activity in FIG. 7a) for liver and muscle. Both parameters seem to relate to lesion severity with a stronger relationship for the delay to the start of type 2 activity than for the increase in echogenicity. In these graphs, the points for liver and muscle overlap.

As noted previously in this specification, several investigators have reported expanding hyperechoic regions in ultrasonic images made during laser irradiation of tissues. Because of the large increase in echogenicity which subsequently decreases when the laser is turned off, it has been postulated that vapor or microbubble formation is responsible for the increase. The type 2 activity in our exposures is characterized by large and dynamic modulation in the amplitude and phase of the signal as seen in FIG. 3b and FIG. 4a. The activity usually starts suddenly and stops immediately when the laser is turned off. This is most likely caused by the appearance and disappearance of highly reflective scatterers such as gas bubbles. Thus, we concluded that the dynamic type 2 activity is caused by vaporization of tissue, and the residual increase in echogenicity after the laser has been turned off is due to remaining gas bubbles or to the dehydration or carbonization of the remaining tissue.

Both residual echogenicity and the delay to the start of type 2 activity are functions of laser power as shown in FIGS. 6–6b. The differences between muscle and liver are likely due to different absorption coefficients for the 805 nm laser energy. The darker liver probably absorbed more of the applied energy, and thus lesions occurred at lower power than in muscle.

The acoustic parameters also changed at lower power levels for liver than for muscle suggesting that they are related to energy absorption and/or lesion development. If type 2 activity is caused by vaporization of tissue, the delay between energizing the laser and the start of type 2 activity should be a function of the total power absorbed by the tissue and the ability to dissipate the heat as the temperature rises. It is known that lesion severity and size is related to the amount of power absorbed and the time of application. Total power absorbed is the product of the laser power applied and the absorption coefficient of the tissue. FIG. 7a shows a strong relationship between lesion severity and the delay to type 2 activity suggesting that this parameter is related to the power absorbed and could be used to predict lesion severity independent of tissue type, color, or optical absorption properties.

Residual echogenicity is probably related to changes in the structure and to reorganization of tissue during coagulation and ablation. In this study, type 2 activity was easy to detect, and the delay to the start was an accurate number. Amplitude, however, was more difficult to quantify accurately and reproducibly.

Periodic type 2 activity has not been reported by others, but resembles signals we see by placing a Doppler sample volume on the end of a wire connected to a vibrating speaker (Hartley, et al. (1991), supra). If the amplitude of the vibrations is less than 0.5 wavelengths (37.5 μm), the loops are not complete circles, and the angle of the arc is proportional to the peak-to-peak excursion of the target. If type 2 activity is caused by creation of gas bubbles, the periodicity could be due to resonance of stable bubbles. Vibrations with resonant frequencies from 500 Hz to 2.5 kHz were detected in 10 of the 22 exposures exhibiting type 2 activity. None were seen with type 1 activity. Because the loops in the Doppler vector are not complete and thus not sinusoidal, the signal will be distorted, and the frequency will not be the same as the Doppler shift expected for the velocity of vibration. Since we sampled at only one range, periodicity could have occurred at other positions along the sound beam in other exposures.

Type 1 activity is characterized by slowly changing phase and amplitude and is concluded to be due to tissue motion combined with small changes in echogenicity. This is consistent with expansion and contraction of tissue due to heating and with coagulation at temperature increases insufficient to cause vaporization.

TABLE I

Summary of Experimental Data

| Laser Power Applied Watts | Exposure Duration Seconds | Maximum Type of Activity (0, 1, 2) | Delay to start of Type 2 Seconds | Increase in Echo Amplitude x Control | Darkness of Lesion Core (if any) |
|---|---|---|---|---|---|
| Muscle | | | | | |
| 13 | 180 | 0 | — | 1 | none |
| 14 | 180 | 1 | — | 1.3 | none |
| 18 | 180 | 1 | — | 1.5 | none |
| 18 | 180 | 1 | — | 3.7 | none |
| 18 | 180 | 2 | 75 | 6.0 | faint |
| 22 | 180 | 2 | 77 | 10.0 | faint |
| 23 | 180 | 1 | — | 2.4 | none |
| Liver | | | | | |
| 4 | 60 | 1 | — | 1.7 | none |
| 4 | 120 | 1 | — | 1.5 | none |
| 4 | 120 | 1 | — | 2.0 | faint |
| 5 | 60 | 2 | 26 | 6.0 | faint |
| 5 | 60 | 2 | 28 | 5.3 | faint |
| 5 | 120 | 1 | — | 2.3 | faint |
| 5 | 120 | 0 | — | 1.5 | faint |
| 5 | 120 | 2 | 104 | 7.5 | dark |
| 6 | 60 | 1 | — | 1.5 | none |
| 6 | 60 | 2 | 18 | 9.0 | dark |
| 6 | 120 | 2 (osc) | 36 | 5.0 | faint |
| 6 | 120 | 2 | 28 | 3.0 | dark |
| 6 | 120 | 2 | 12 | 4.5 | dark |
| 6 | 180 | 2 (osc) | 22 | 1.7 | dark |
| 6 | 120 | 2 | 26 | 8.0 | faint |
| 7 | 120 | 1 | — | 2.0 | faint |
| 7 | 120 | 2 (osc) | 7 | 6.0 | faint |
| 8 | 60 | 2 (osc) | 2 | 10.0 | black |
| 8 | 60 | 2 | 5 | 7.0 | dark |
| 9 | 100 | 1 | — | 0.7 | none |
| 10 | 60 | 2 | 3 | 10.0 | black |
| 11 | 30 | 2 | 3 | 3.0 | black |
| 12 | 60 | 2 (osc) | 5 | 12.0 | black |

TABLE I-continued

Summary of Experimental Data

| Laser Power Applied Watts | Exposure Duration Seconds | Maximum Type of Activity (0, 1, 2) | Delay to start of Type 2 Seconds | Increase in Echo Amplitude x Control | Darkness of Lesion Core (if any) |
|---|---|---|---|---|---|
| 13 | 60 | 2 (osc) | 2 | 14.5 | dark |
| 15 | 60 | 2 (osc) | 2 | 12.5 | dark |
| 17 | 60 | 2 (osc) | 4 | 11.0 | faint |
| 17 | 60 | 2 (osc) | 2 | 12.0 | black |
| 19 | 60 | 2 (osc) | 2 | 6.0 | black |

2. Experimental Results Using an Eight-Range-Gate Pulsed Doppler Detector a. The Development of an Analog-Digital Hybrid Multiple-Range-Gate Pulsed Doppler System The ultrasound system of FIG. 2a comprises a 1.2 mm diameter 20 MHz ultrasound transducer 64, analog eight-range-gate pulsed Doppler detector 60a, high-speed 16-channel 12-bit A/D conversion board 91 with data acquisition software, and digital signal analyzer 96.

Echo-Doppler transmitter 74 generates eight cycle bursts of ultrasound that are transmitted by transducer 64 into a target, say a sample of tissue, and the echoes returned from the tissue are received by the same transducer 64. The echoes are processed by detector 60a, which retains both amplitude and phase information in sound echoes, as supposed to only amplitude information in the non-Doppler ultrasound studies. Two quadrature Doppler range-phase signals, x(d,t) (79) (Eq. (9)) and y(d,t) (77) (Eq. (10)), are produced, where d is the range along the sound beam. The range-phase signals are sampled after eight time delays. The sampling results in eight pairs of orthogonal components that form eight phase vectors reflecting activity at the eight tissue depths. The orthogonal components can be described by:

$$I(d_i, t) = A(d_i, t) \cos(\Phi(d_i, t)) \quad (15)$$

$$Q(d_i, t) = A(d_i, t) \sin(\Phi(d_i, t)) \quad (16)$$

$$i = 1, 2, \ldots, 8$$

where t is time and $d_i$ is the distance between the transducer tip and the tissue depth pointed to by the i-th range-gate pulse. $A(d_i,t)$ is the amplitude while $\Phi(d_i,t)$ is the phase (in radians) of the received echoes at $d_i$. $I(d_i,t)$ and $Q(d_i,t)$ are called in-phase (I) and quadrature-phase (Q) Doppler signals, respectively. In our detector, we made space between two consecutive range gates equal. The position of the first range-gate pulses and the equal space between two consecutive range-gate pulses are adjustable.

For given $I(d_i,t)$ and $Q(d_i,t)$, the amplitudes and phases of the phase vectors can be computed as:

$$A(d_i,t) = \sqrt{[I(d_i,t)]^2 + [Q(d_i,t)]^2} \quad (17)$$

$$\Phi(d_i,t) = \tan^{-1}\left(\frac{Q(d_i,t)}{I(d_i,t)}\right). \quad (18)$$

If $I(d_i,t)$ and $Q(d_i,t)$ are shown in eight X–Y plots (X is $I(d_i,t)$ and Y is $Q(d_i,t)$), the radii are the amplitudes $A(d_i,t)$, representing echogenicity of the tissue reflectors, while the angles between the current positions of the phase vectors and the x axes are the phases $\Phi(d_i,t)$, describing the position of the reflectors. If a reflector at one depth moves, its corresponding phase vector rotates. The faster the reflector moves, the faster its corresponding vector rotates. With 20 MHz transducer 64 used in a preferred embodiment of the present invention, one revolution of the phase change ($2\pi$) equals 37.5 μm displacement of the reflector. The rotation direction tells whether the reflector is approaching or leaving the ultrasound transducer. For the detector discussed herein, counterclockwise rotation always means the target is moving towards the transducer, and clockwise rotation means the opposite direction.

The derivative of $\Phi(d_i,t)$ with respect to time yields the Doppler shift. That is:

$$d\Phi(d_i,t)/dt = 2\pi f_d(d_i,t), \qquad (19)$$

with $f_d(d_i,t)$ being the Doppler shift frequency in hertz.

If a phase vector rotates in one direction and completes one circle in one second, the Doppler shift frequency is one Hz. In addition to these 16 signal outputs, the detector also outputs a range-phase signal y(d,t).

This type of pulsed Doppler detector has been employed in the study of blood flow and myocardial thickening (see FIG. 1). In these applications, high-pass filters are used to remove low Doppler shift frequency components as velocity of the motion is relatively high. In the detector according to the present invention, however, these high-pass filters were not implemented because a Doppler shift frequency as low as 0 Hz (direct current level) was desired to probe any motion, no matter how slow.

Sixteen analog two-pole 50 Hz low-pass active filters 86a were implemented to filter the 16 outputs 85 ($I(d_i,t)$, $Q(d_i,t)$, (i=1, . . . ,8)) for the anti-aliasing purpose, as the outputs were to be digitally sampled. Consequently, the maximum Doppler shift frequency that the detector could output was 50 Hz, representing 1.95 mm/s motion.

All 16 filtered signal outputs 89 were simultaneously sampled by high-speed 16-channel 12-bit A/D conversion board 91 (Data Translation DT2801A, Mass.). The effective sampling resolution was 11 bits, as one bit was used for bipolarity of the ultrasound signals. Sampling was controlled by a data acquisition software (Data Translation Global Lab™) run on a 486/33MHz based personal computer 90 (having a color monitor 92), and the data were saved on hard disk 94 of computer 90 for off-line processing and analysis.

To visualize and analyze the sampled signals, we developed a digital analyzer 96 with a graphical user interface by utilizing MATLAB™ (The MathWorks, Mass.) and its toolboxes. Analyzer 96 could effectively make any desirable computation on a large data volume and display simultaneously multiple two-dimensional and three-dimensional graphics including trajectories of the phase vectors shown in X–Y or X–Y–Z display. Analyzer 96 could also perform spectral analysis and many other functions.

b. Evaluating Motion Detection Sensitivity of the Pulsed Doppler Detector

Figure 8:
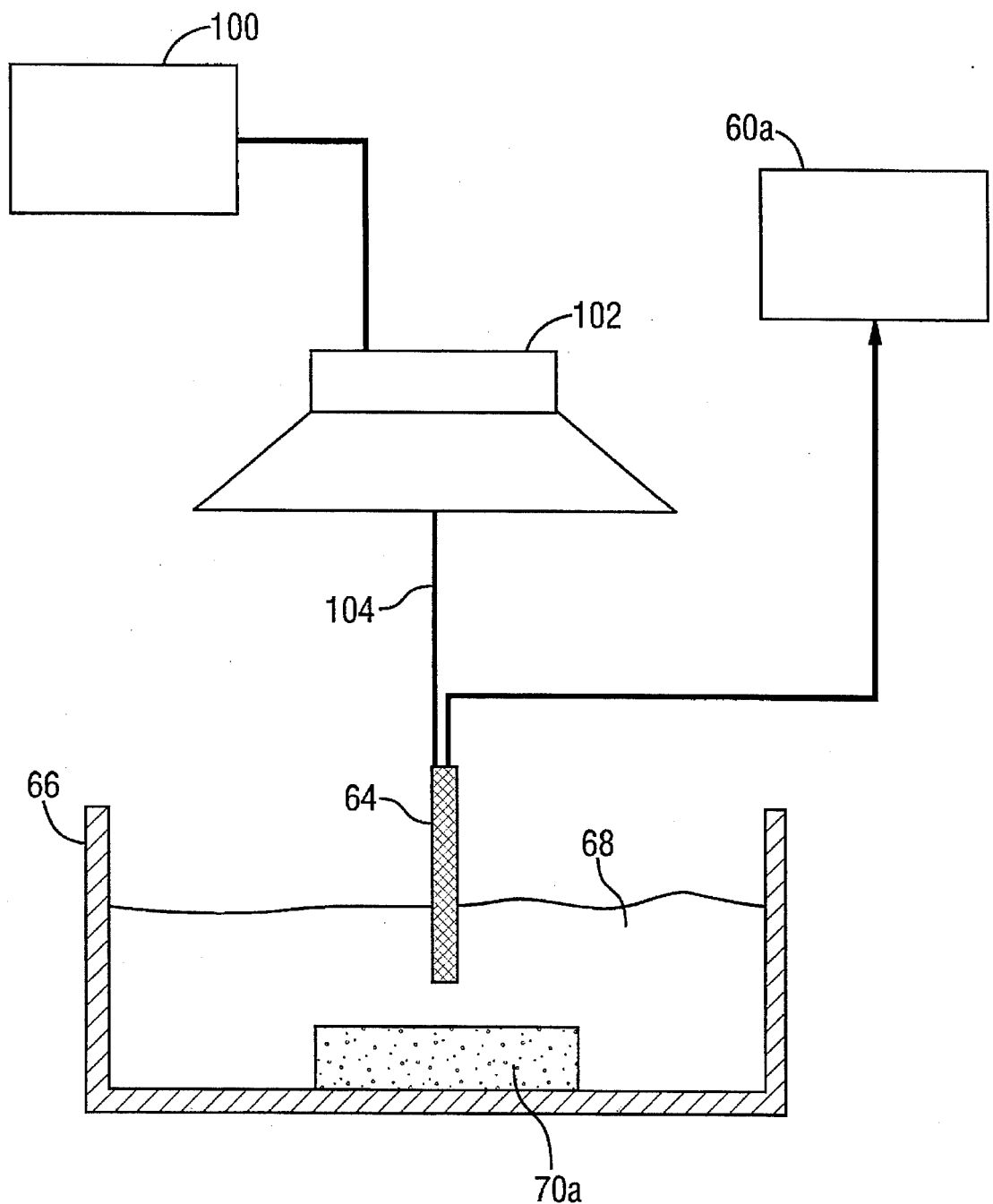
FIG. 8 is a schematic diagram of the experimental setup for evaluating motion detection sensitivity of the eight-range-gate pulsed Doppler detector.

FIG. 8 depicts the setup of the motion detection sensitivity experiments. A piece of sponge 70a, used as a tissue model, was submerged in water 68 in tank 66. The water provided acoustic coupling for ultrasound transducer 64. To create very slow relative motion between transducer 64 and sponge 70a, transducer 64 was firmly attached to a piece of straight metal wire 104 glued on 3" speaker 102. Speaker 102 was driven by digital function generator 100 (Wavetek 154) capable of generating very low frequency (e.g. 0.0001 Hz) triangular waveform. Transducer 64 was driven by speaker 102 to move back and forth very slowly as if the sponge were moving and the transducer held still. The peak-to-peak amplitude of function generator 100 was set to 1.6 V and the motion velocity of transducer 64 could be varied by changing the frequency of the triangular waveform.

The range-phase ultrasound signal, y(d,t), was displayed on oscilloscope 78 along with the eight range-gate pulses. The video image of the display, along with the time information generated by time code generator 98 (FOR.A VTG-55B, Japan), were taken by video camera 80 and recorded on video camera recorder 88 (Panasonic AG-7355). In this experiment, the first range-gate pulse of the detector was positioned to point to 1 mm beneath the surface of sponge 70a while the space between two consecutive range-gate pulses was 0.5 mm. The 16 filtered outputs 89 of detector 60a were sampled at 10 Hz.

Figure 9:
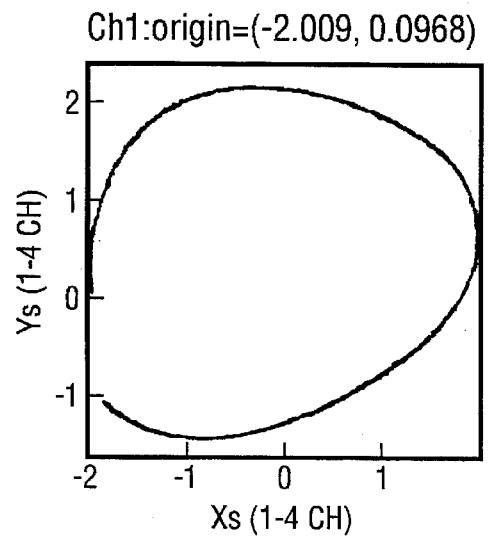
FIGS. 9–9g show one set of the results obtained in motion detection sensitivity experiments conducted using the apparatus of FIG. 8 showing, in X–Y plots, how the I and Q Doppler signals at the eight different tissue depths changed with time.
Figure 9A:
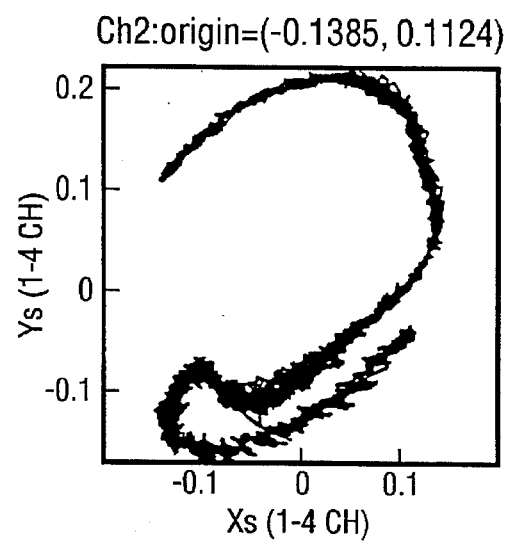
Figure 9B:
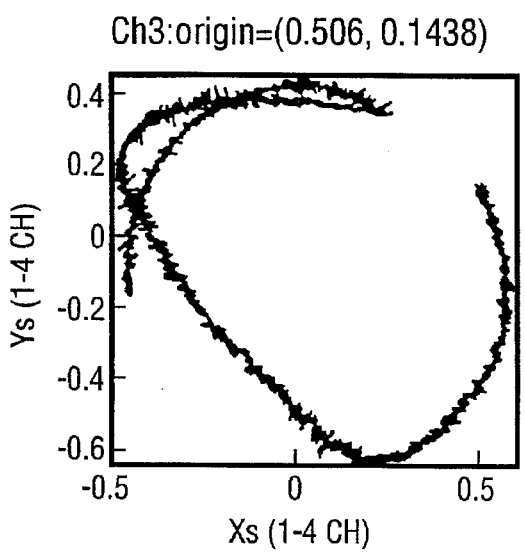
Figure 9C:
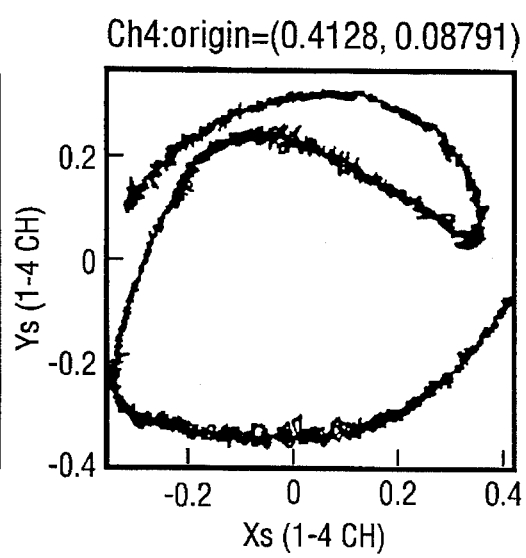
Figure 9D:
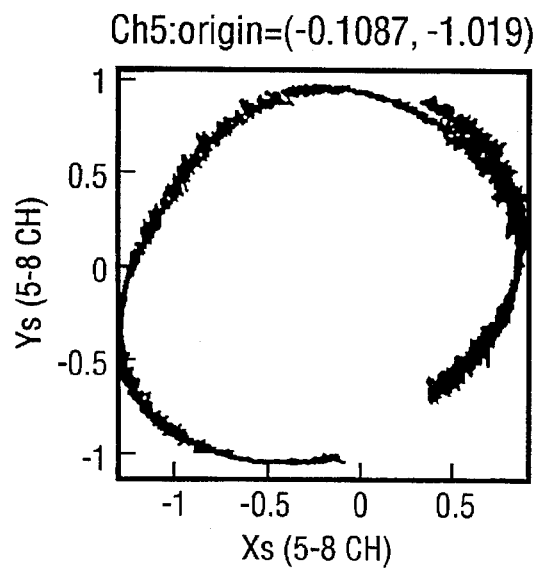
Figure 9E:
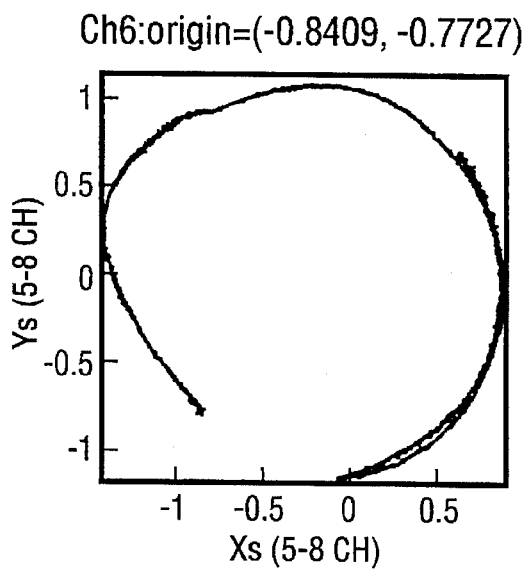
Figure 9F:
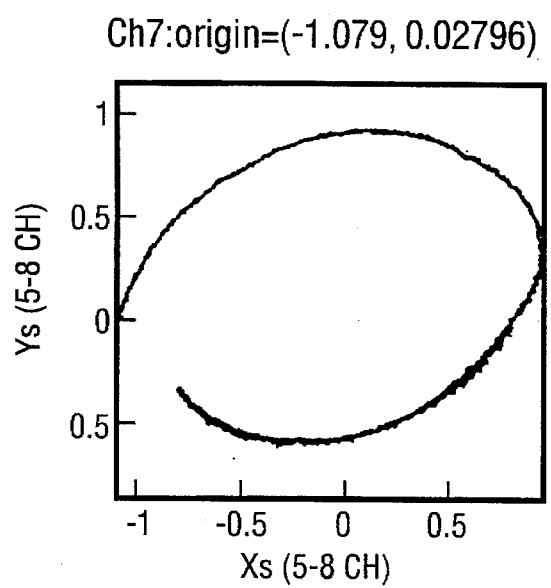
Figure 9G:
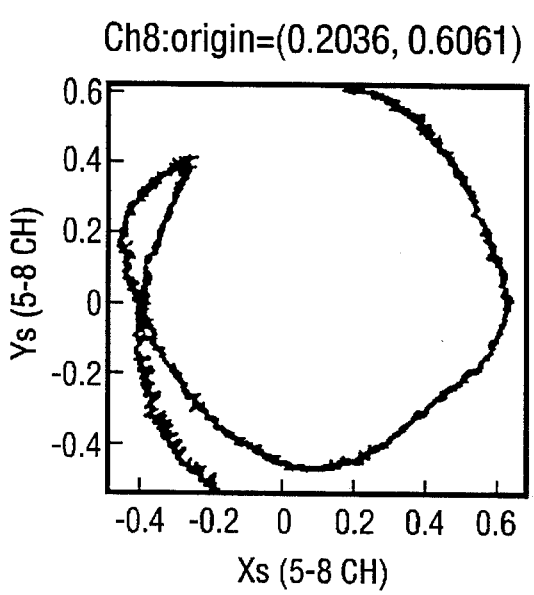

FIGS. 9–9g is one of the experimental results, showing the I and Q Doppler signals, in volts, at the eight different sponge depths as X–Y plots. The experiment lasted 15 minutes and the frequency of the triangular waveform was 0.004 Hz. One can see that the relative motion was sensed at all the depths as all the plots show circular trajectories of the phase vectors.

Figure 10:
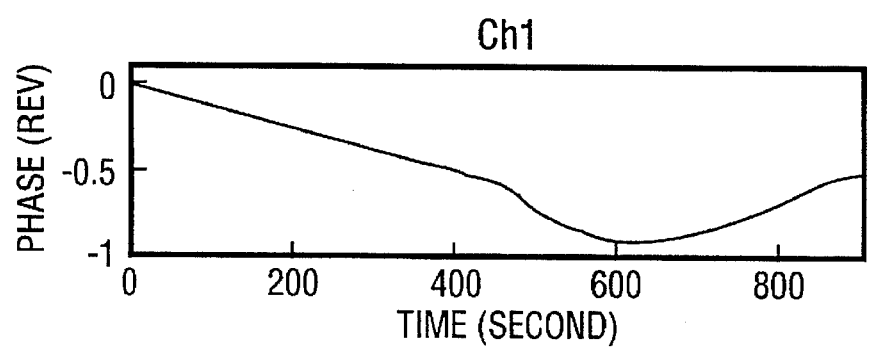
FIGS. 10–10g show the corresponding phase change with respect to time for the results shown in FIGS. 9–9g.
Figure 10A:
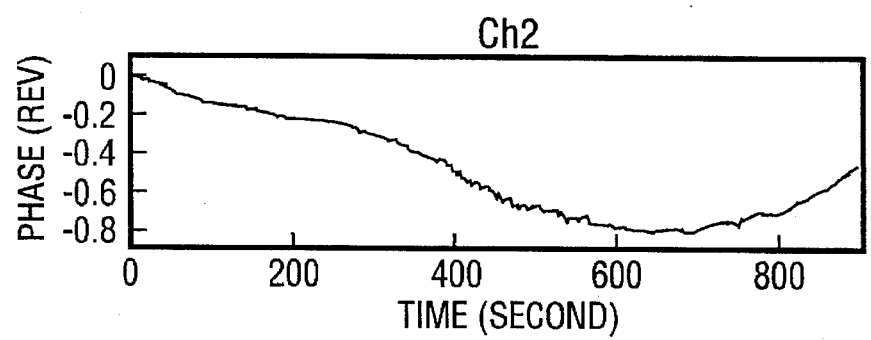
Figure 10B:
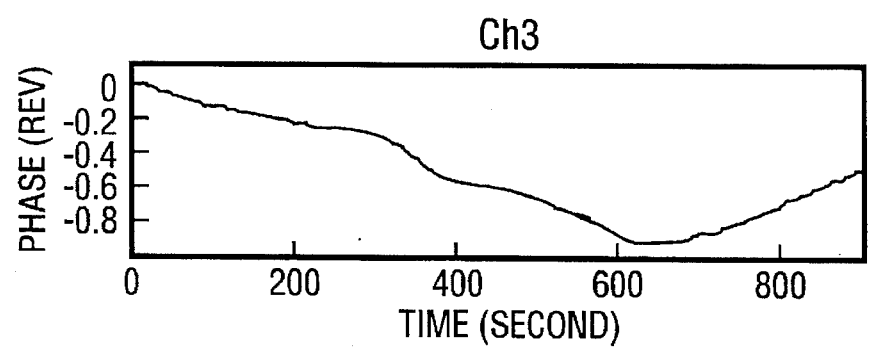
Figure 10C:
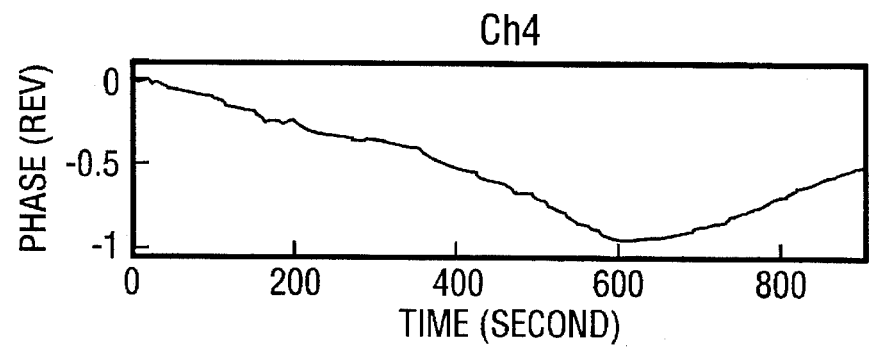
Figure 10D:
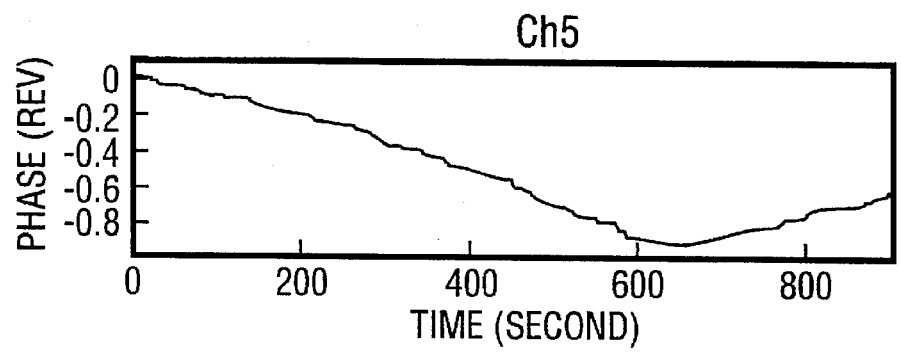
Figure 10E:
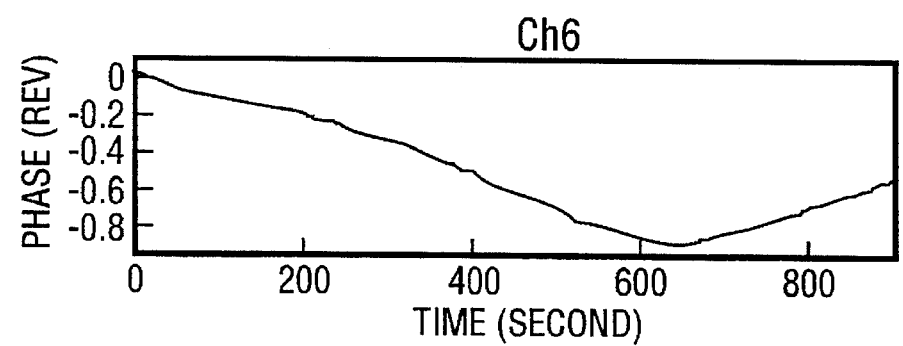
Figure 10F:
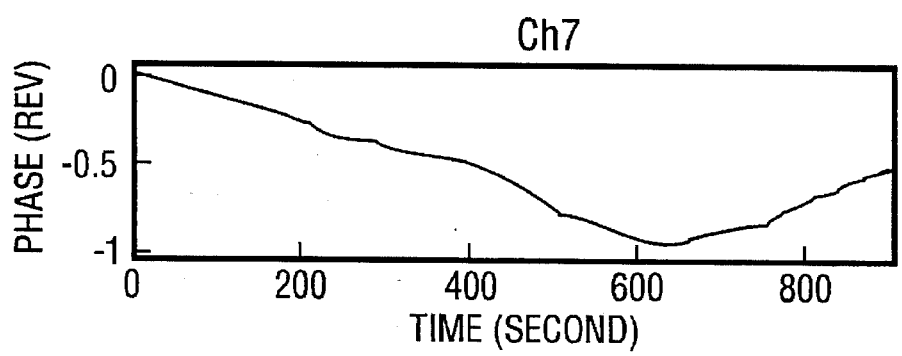
Figure 10G:
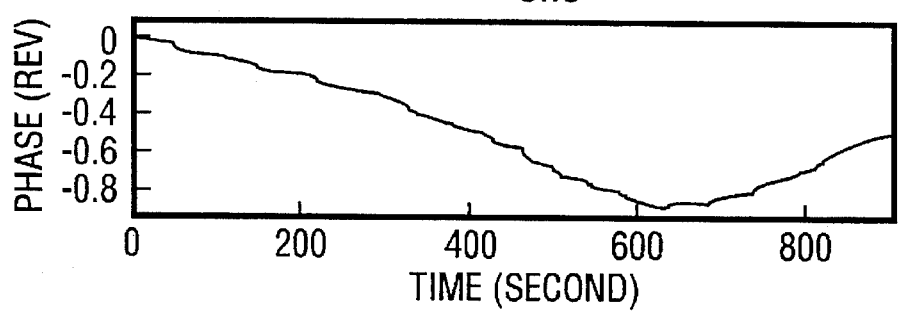

FIGS. 10–10g depict the change in phases, in revolutions (note one revolution =37.5 μm), with respect to time at the eight depths (ranges 1–8 respectively). The phase changes were computed in terms of the initial phases, respectively. In other words, the initial position of the phase vectors was regarded as zero phase, producing equal basis for distance calculation. Integration of the phases gave the distance that transducer 64 traveled, with the initial position of transducer 64 when the A/D conversion 91 started being zero distance. The phases were negative (i.e., the phase vectors were rotating clockwise). The motion changed the direction at 624 seconds when transducer 64 reached its maximum displacement in one direction and started to move in the opposite direction. This can be seen in FIGS. 9–9g, where all the trajectories of the phase vectors changed from clockwise rotation to counter-clockwise rotation. At range gates 1 and 7, the direction change cannot be differentiated well due to the overlap of the trajectories of the phase vectors in both directions, which would happen to all the range gates should every condition be perfect.

Figure 11:
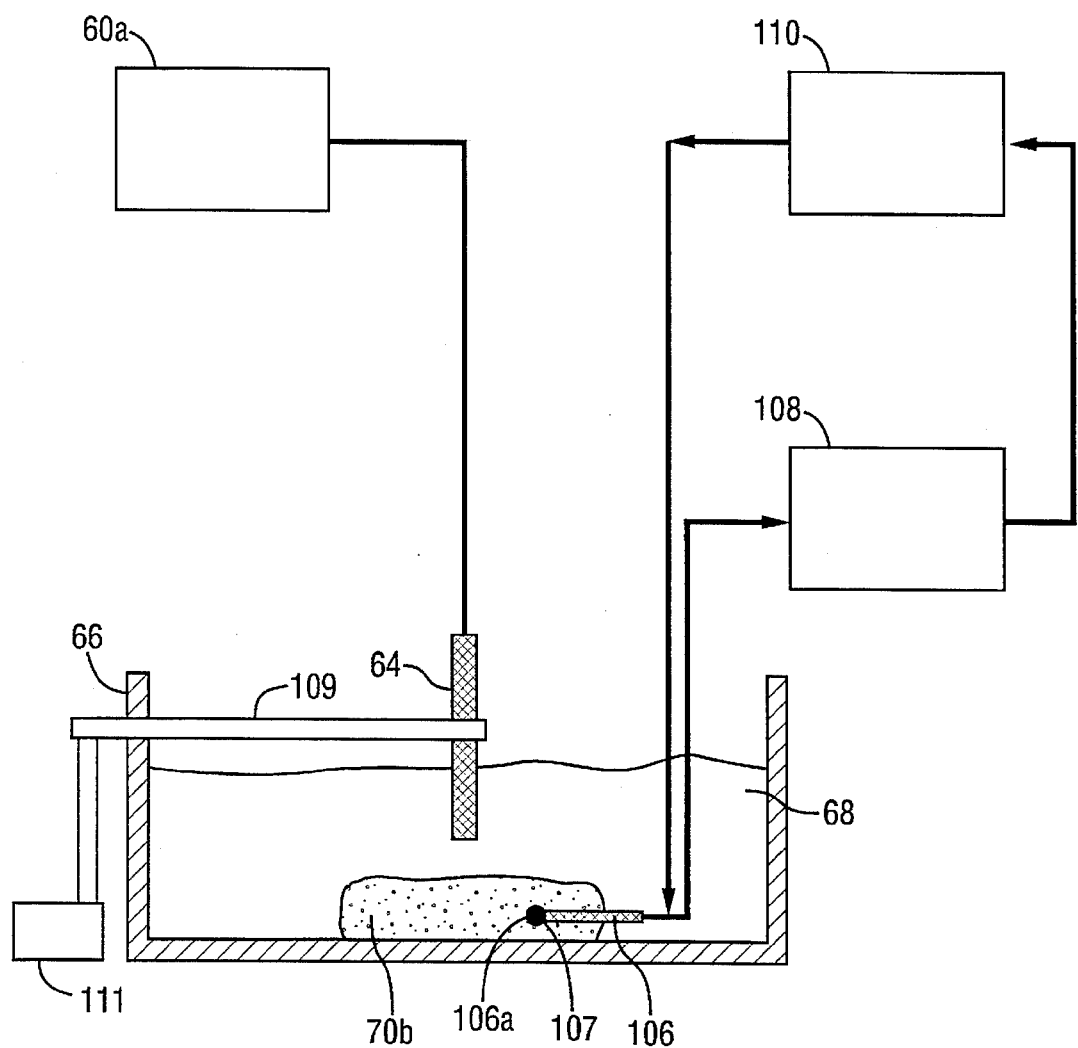
FIG. 11 illustrates a block diagram of the experimental setup for detecting thermal response in a fresh sample of beef muscle being heated by a thermistor according to the present invention.

Slight measurement errors were observed among the range gates. The mean maximum displacement was 33.47 μm with a standard deviation of 1.78 μm, happening at a mean time of 624.2 seconds with a standard-deviation of 1.458 seconds. In 15 min (900 s), the mean and standard deviation of total two-directional displacement were 48.17 μm and 3.01 μm, respectively. The mean measured velocity of the transducer motion was 0.0535 μm/s, which gauged motion detection sensitivity of the ultrasound detector 60a. We conclude that this eight-range-gate detector is capable of detecting a motion at least as slow as 0.0535 μm/s. One should be aware that this is not the limit sensitivity of the detection, however.

c. Experiments for Detecting Thermal Response in Beef Muscle Samples Being Heated by a Thermistor FIG. 11 shows the setup of the experiment for detecting thermal response in a fresh sample of beef muscle 70b. Tissue 70b was submerged in water 68 in tank 66. Glass-coated thermistor probe 106 (Thermometrics P100, N.J.) was inserted into the tissue horizontally about 3.5 mm beneath the surface of tissue 70b to heat the tissue by direct thermal conduction. Thermistor tip 106a was in spherical shape with a diameter of 0.9 mm. The temperature of probe 106 was measured by thermocouple 107 glued on the tip 106a. Thermocouple 107 was connected to temperature scanner 108 (Azonix ScannerPlus, Mass.) that displayed the current temperature as well as sent it to feedback temperature controller 110 for maintaining a user-defined temperature. The maximum power rating of thermistor 106 was 0.1 W and, consequently, the maximum achievable tissue temperature in the experiment was 76° C.

Ultrasound transducer 64 was firmly held by holder 109 mounted on X–Y–Z position adjuster 111 that was adjusted, while we were watching the range-phase signal y(d,t) on the oscilloscope 78, so that thermistor tip 106a was right on the ultrasound beam path. The last range-gate pulse was pointing to the depth where thermistor tip 106a was located. The space between two consecutive range gates was 0.5 mm and, therefore, the first range-gate pulse was pointing to slightly beneath the surface of tissue 70b. The sampling rate of the A/D conversion was 30 Hz. Thermistor 106 was turned on 10 seconds after the A/D conversion started to collect ultrasound signal baseline. The initial tissue temperature sensed by thermocouple 107 was 24° C.

Figure 12D:
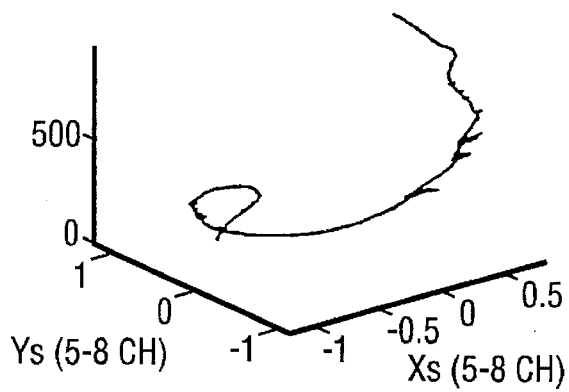
FIGS. 12–12g show trajectories of phase vectors three-dimensionally at eight tissue depths for the experimental set up of FIG. 11, with the thermistor operated at 45° C.
Figure 12E:
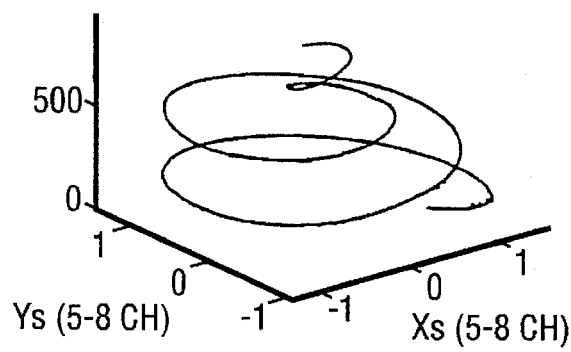
Figure 12F:
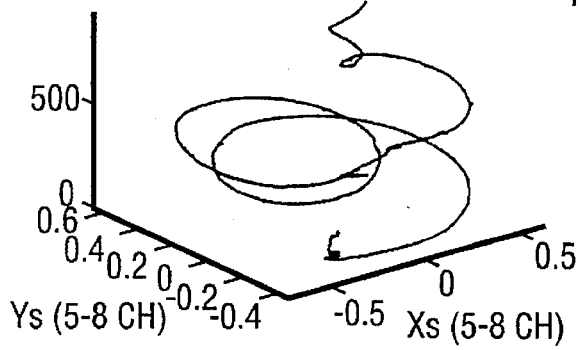
Figure 12G:
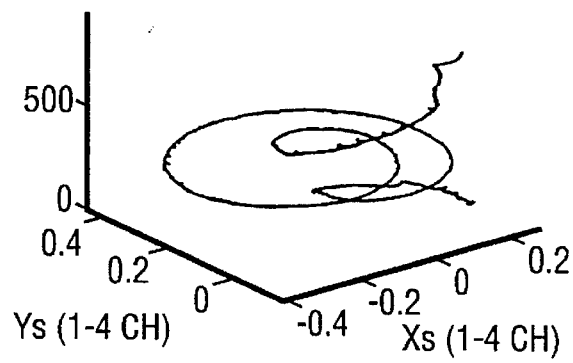
Figure 13:
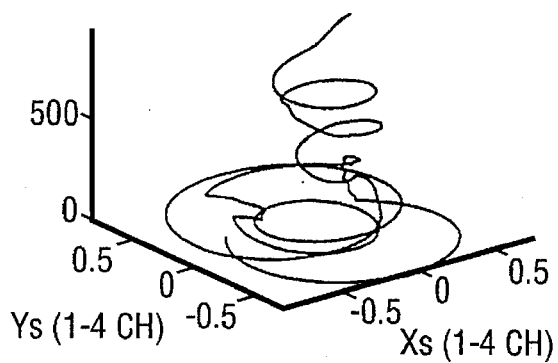
FIGS. 13–13g show trajectories of phase vectors three-dimensionally at eight tissue depths for the experimental set up of FIG. 11, with the thermistor operated at 75° C.
Figure 13A:
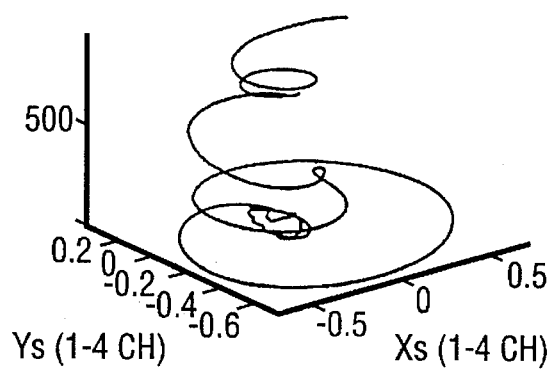
Figure 13B:
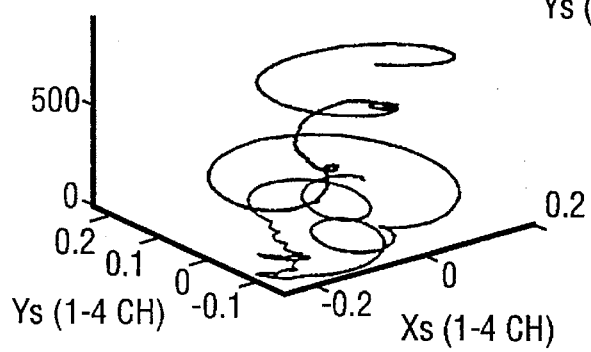
Figure 13C:
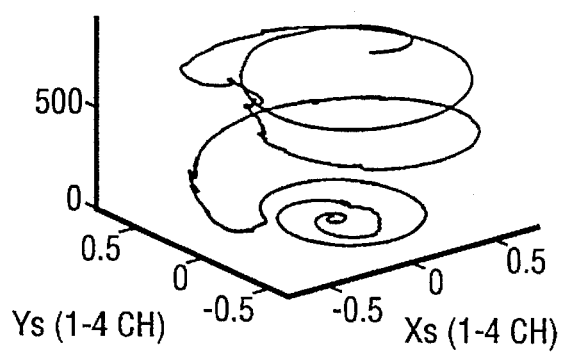
Figure 13D:
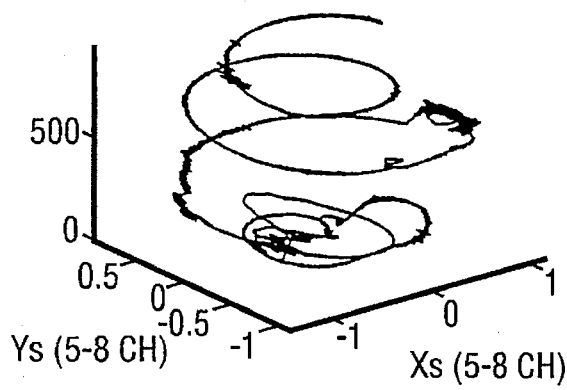
Figure 13E:
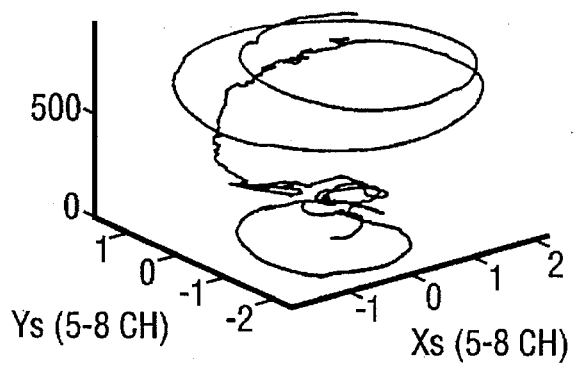
Figure 13F:
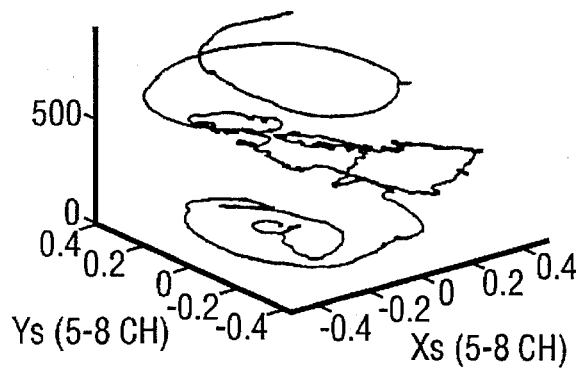
Figure 13G:
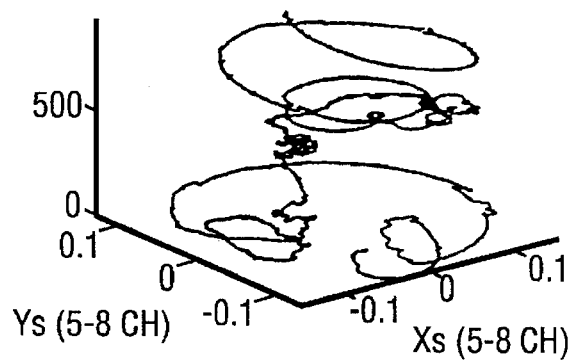

FIGS. 12–12g and 13–13g demonstrate two of the thermistor experimental results three-dimensionally. They show the trajectories of the phase vectors at the eight depths versus time (X axis is $I(d_i,t)$ in volts, Y axis is $Q(d_i,t)$ in volts, and Z axis is time, t, in seconds). In FIGS. 12–12g, the temperature setpoint was 45° C. and it took 30 seconds for the temperature to reach the setpoint from the initial temperature. The thermistor was turned off at 12 minutes and 33 seconds, three minutes before the experiment finished. In FIGS. 13–13g the temperature setpoint was 75° C. and it took 2 minutes and 40 seconds for the temperature to reach the setpoint from the initial temperature. The thermistor was turned off at 10 minutes and 20 seconds, five minutes 12 seconds before the experiment finished. According to FIGS. 12–12g and 13–13g, once the thermistor was turned on, all eight phase vectors started rotating immediately and simultaneously in counterclockwise direction. This fact indicates that the tissue at the eight depths along with the sound beam was leaving thermistor tip 106a or equivalently, approaching ultrasound transducer 64. The motion was tissue thermal expansion. The closer a range gate was to thermistor tip 106a, the larger the motion (this is especially apparent in FIGS. 12–12g). The motion at the range gates 7 and 8 was the largest in both cases, indicating that the tissue around thermistor tip 106a was the hottest and consequently was coagulated (in the case of 75° C.) first compared to the tissue at the other depths. These results indicate that one can use the motion information to determine tissue thermal damage status at different tissue depths.

Another important observation is that a thermistor temperature of 75° C. caused significantly more motion than a temperature of 45° C. did. This can be seen if one compares motion gate-by-gate between FIGS. 12–12g and FIGS. 13–13g. This result is logical as a higher temperature causes more tissue thermal expansion than a lower temperature does. It is concluded that tissue temperature at different depths can be determined according to the motion at different depths. In other words, temperature temporal and spatial profiles can be determined based on the Doppler signals.

Finally, FIGS. 12–12g and 13–13g show that once the thermistor was turned off, all eight phase vectors quickly and simultaneously changed rotation direction from counterclockwise to clockwise. This motion is tissue thermal contraction, happening once the heating source disappears.

It should be pointed out that the motion pattern in all the thermistor experiments was type 1 activity, as defined previously in the study of using the single-range-gate pulsed Doppler detector. This was expected as the tissue temperature was relatively low (maximum 75° C.) and tissue was coagulated, not ablated.

We should emphasize that 45° C. is not the lowest limit temperature the ultrasound system can detect. It is low enough, though, to show that the ultrasound system can be used in low-temperature thermal treatment, such as hyperthermia.

The motions seen in the thermistor experiments were caused by the heat generated by the thermistor and therefore they represented thermal response in the heated tissue. There were slow motions at different tissue depths. The characteristics of the motions at multiple tissue depths, including the small velocity, the directions and the concurrent occurrence and timing of the motions with the events of turning the thermistor on or off, indicate that the motions were tissue motions. That is, the ultrasound signals represent tissue thermal expansion and contraction. When the thermistor was on, the tissue was expanding due to the heat. Once the heating source was off, the tissue contracted.

Figure 14:
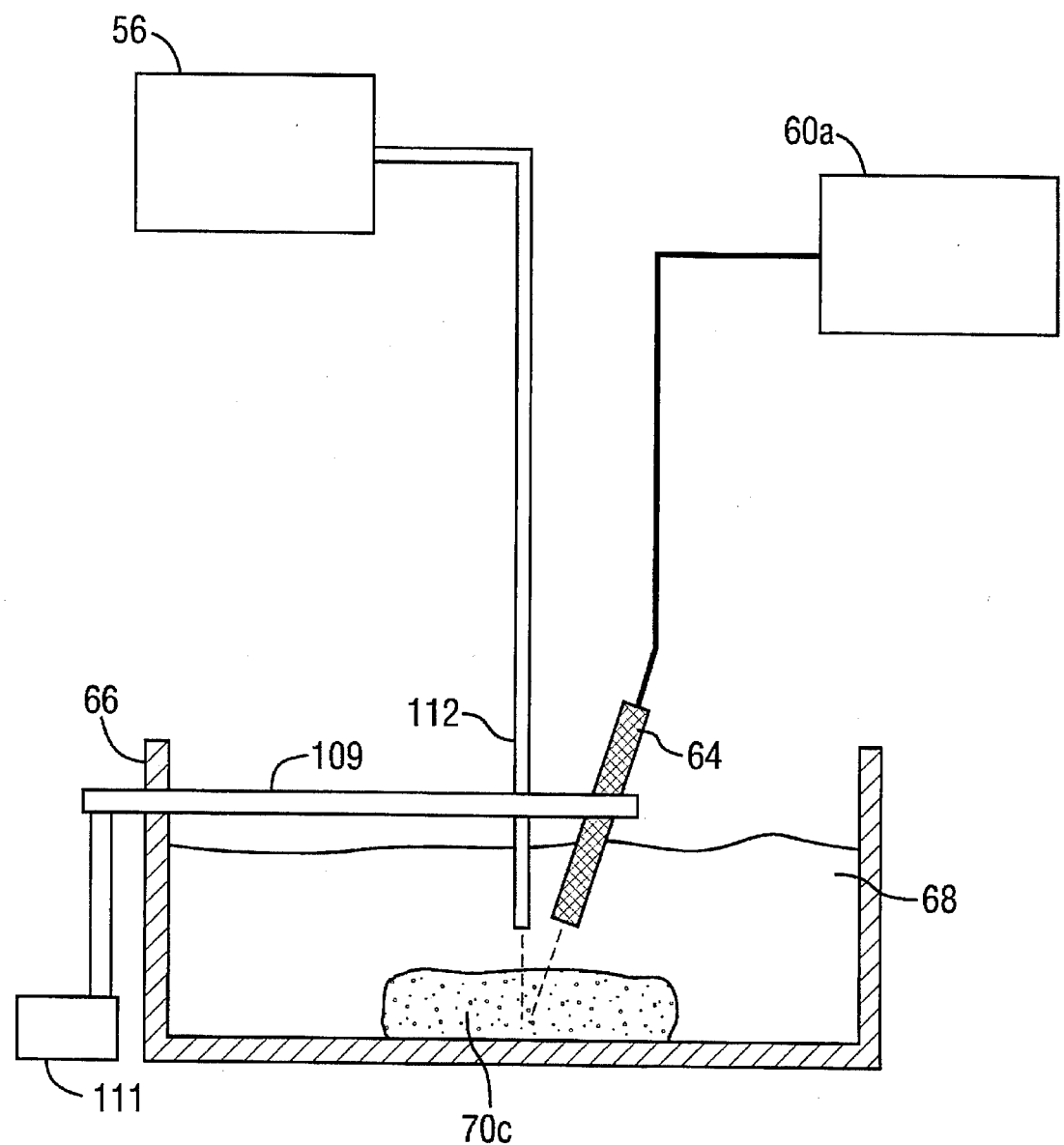

We conclude that our ultrasound system can sensitively detect tissue thermal response due to temperature at least as low as 45° C. generated by any thermal modalities. As tissue thermal expansion and contraction occur in any type of tissue in response to heat generated by any types of thermal modalities, our ultrasound system can be used in any type of thermal therapy, including hyperthermia, thermal coagulation and ablation.

d. Experiments for Detecting Thermal Response in Canine Liver Samples Being Irradiated by Laser FIG. 14 depicts another embodiment of the present invention used as the setup of the experiments involving use of Doppler ultrasound system 60a for detecting thermal response in fresh samples of canine liver being irradiated by a 1064 nm Nd:YAG laser 56. Optical fiber 112 and ultrasound transducer 64 were angled at 8°, making the laser path and ultrasound path intersect each other from the tissue surface to a depth of about 5 mm. Fiber 112 and ultrasound transducer 64 were held together by holder 109 mounted on X–Y–Z position adjuster 111. The distance between the tips of transducer 64 and fiber 112 and the surface of tissue 70c was about 3 mm. The laser energy was deposited through optical fiber 112 of 600 µm core diameter to tissue 70c with a surface spot size approximately 1.5 mm in diameter. Before the experiments, the fiber efficiency was measured for computing actually delivered laser power. The first range gate was pointing to 1 mm beneath the tissue surface and the space between two consecutive range gates was 0.5 mm. The A/D sampling rate was 100 Hz and each experiment lasted three minutes.

Figure 15:
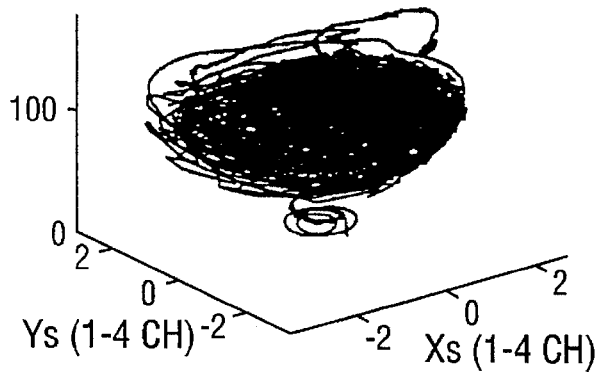
FIGS. 15–15g show trajectories of phase vectors three-dimensionally at eight tissue depths for the experimental set up of FIG. 14.
Figure 15A:
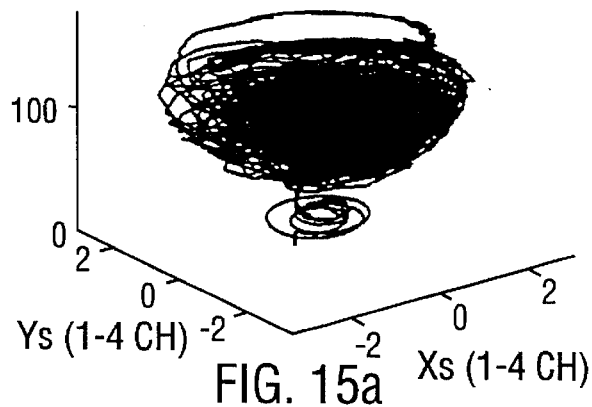
Figure 15B:
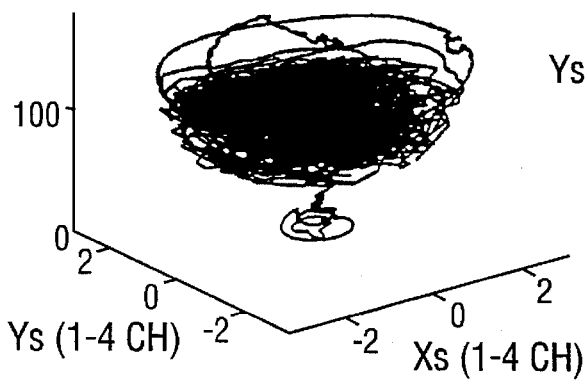
Figure 15C:
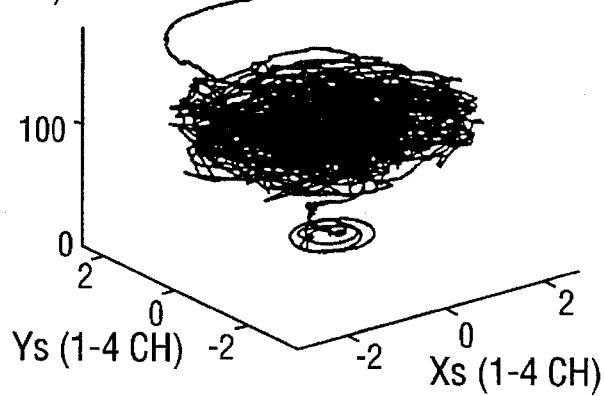
Figures 15D, 15E, 15F, 15G:
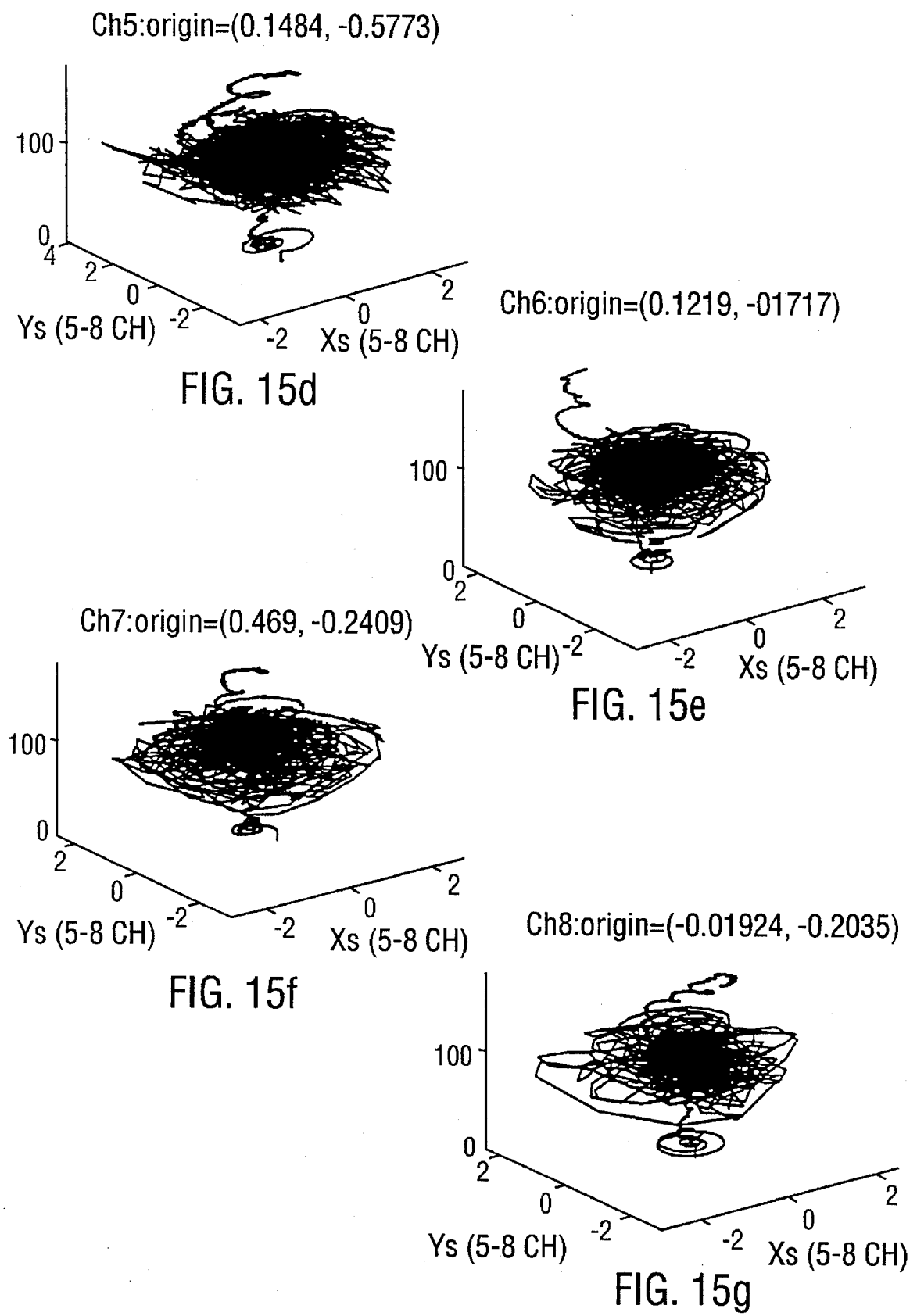

FIGS. 15–15g show one of the laser experimental results three-dimensionally as trajectories of the phase vectors at the eight tissue depths versus time (X axis is $I(d_i,t)$ in volts, Y axis is $Q(d_i,t)$ in volts, and Z axis is time, t, in seconds). The delivered laser power was 10 W. The laser was turned on 10 seconds after the A/D conversion was activated (the 10-second data were obtained for generating ultrasound signal baseline information). The laser was turned off at 120 seconds, one minute before the end of the experiment.

The result contains both type 1 activity and type 2 activity. Before a time of 92 seconds (which can be determined based on plots of I versus time or Q versus time, not shown), all of the phase vectors slowly rotated in counterclockwise direction and showed slow variations in phase and small changes in amplitude, which are the key characteristics of type 1 activity. This kind of behavior of the phase vectors was similar to that of the phase vectors in the thermistor experiments. The behavior represents tissue thermal expansion and indicates that the tissue temperature was relatively low and the tissue was being coagulated, not ablated.

The tissue surface along the laser beam exploded at time 92 seconds (again, the timing can be determined based on plots of I versus time or Q versus time, not shown). Concurrently, the behavior of all the phase vectors suddenly changed from type 1 activity to type 2 activity. That is, the phase vectors demonstrated large variations in phase and amplitude, which are the major characteristics of type 2 activity. Also, the amplitudes of ultrasound signals were much larger than those before the explosion. It is known that tissue explosion requires high pressure inside the tissue generated by high temperature and a rapid increase of temperature. Therefore, type 2 activity represents high tissue temperature and resulting tissue ablation.

Once the laser was turned off at 120 seconds, type 2 activity stopped immediately and type 1 activity resumed. However, the rotation direction of all the phase vectors was clockwise instead of counterclockwise, which was the case before type 2 activity took place. These results indicate that tissue temperature decreased quickly once the heating source (the laser) was turned off and tissue thermal contraction occurred, similarly to the behavior of those phase vectors in the end of the thermistor experiments.

These laser experimental results show that the Doppler ultrasound system can be used to differentiate tissue coagulation (type 1 activity) and tissue ablation (type 2 activity) in real-time. Furthermore, the Doppler ultrasound signals can also be employed to determine in real-time temporal and spatial distribution of tissue temperature and tissue thermal damage status.

DETAILED DESCRIPTION OF THE PREFERRED EMBODIMENTS

Figure 2A:
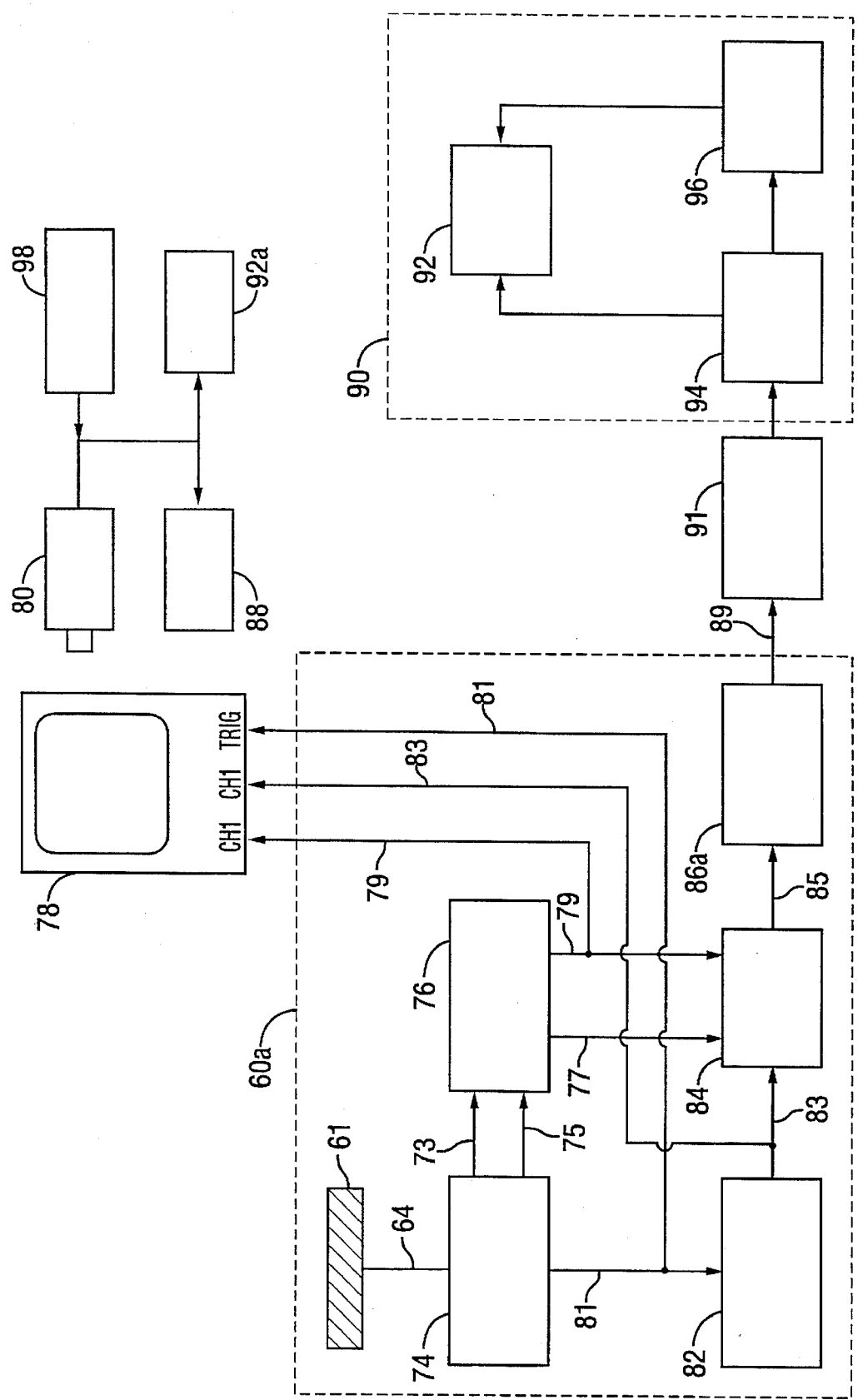
FIG. 2a illustrates a block diagram of an analog-digital hybrid eight-range-gate pulsed Doppler ultrasound system according to the present invention as connected to apparatus for displaying and recording ultrasound signals.

As demonstrated above, the configurations of FIGS. 2 and 2a have proved to be useful in detecting tissue thermal response and in distinguishing between two different types of tissue response resulting from thermal treatment. Type 1 activity was determined to be due to coagulation of tissue, whereas type 2 activity was determined to correspond to ablation of tissue. The present invention uses essentially the configuration of FIGS. 2 (single-range-gate) and 2a (multiple-range-gate) to determine the extent and geometry of tissue thermal damage. The present invention also uses these configurations to determine tissue temperature at multiple depths. The damage status and tissue temperature are used to automatically or manually control thermal modalities.

Figure 16:
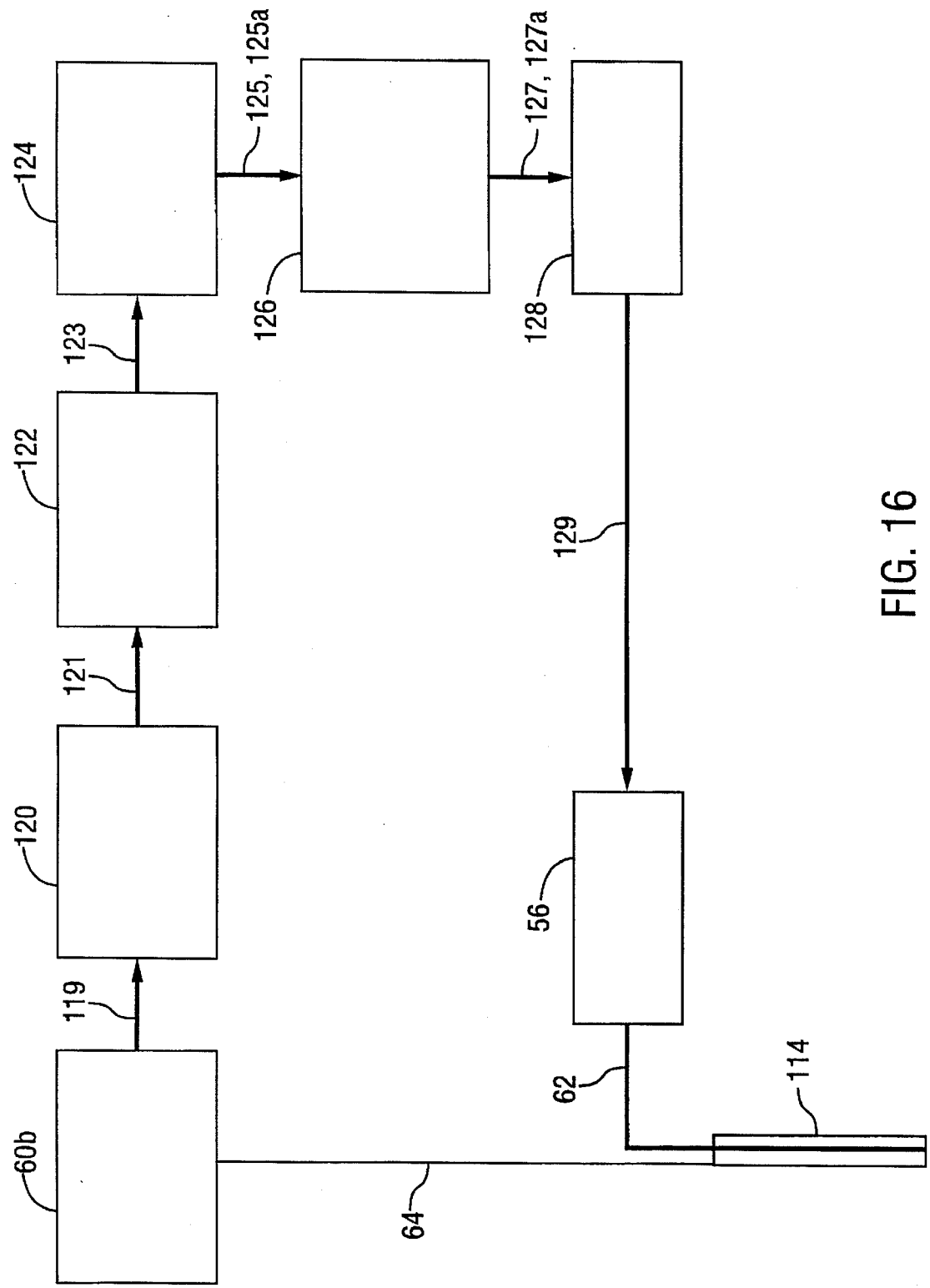
FIG. 16 is a block diagram of apparatus for noninvasive, Doppler ultrasound-guided real-time automatic control of the extent and geometry of tissue damage in thermal therapy according to the present invention.

A block diagram of an apparatus according to the present invention is shown in FIG. 16. The exemplary Doppler ultrasound-guided, real-time automatic control system shown in FIG. 16 uses a laser as the thermal modality, and comprises N-range-gates pulsed Doppler detector 60$b$ with ultrasound transducer 64, 16-bit 2N channel high speed analog-to-digital converter 120, N identical Tissue Background Signal Elimination Modules 122, N identical Doppler Signal Processing Modules 124 and N identical Tissue Temperature and Thermal Damage Determination Modules 126, Laser Control Module 128 and laser 56 coupled to fiber optic 62. The identical modules run in parallel to process Doppler signals from up to N different range gates simultaneously. Other thermal modalities include, but are not limited to, ultrasound, thermistors, and electromagnetic wave.

The detailed configuration of the N-range-gates pulsed Doppler detector 60$b$ is similar to the eight-range-gate pulsed Doppler detector we have constructed, shown in FIG. 2a, except the number of range gates is N. N is an arbitrary positive integer, and larger N values yield better spatial resolution on tissue temperature and thermal damage profiles, but the hardware implementation may cost more.

16-bit 2N-channel high-speed analog-to-digital converter 120 converts N pairs of analog Doppler quadrature signals 119 ($I(d_i,t)$ and $Q(d_i,t)$) to digital format ($i=1,2,\ldots,N$, and $d_i$ is the distance between the tip of the ultrasound transducer to the tissue depth pointed to by the i-th range gate). A sampling rate of 1,024 Hz per A/D channel is used to yield sufficient frequency resolution in power spectrum analysis in Doppler Signal Processing Module 124.

Figure 17:
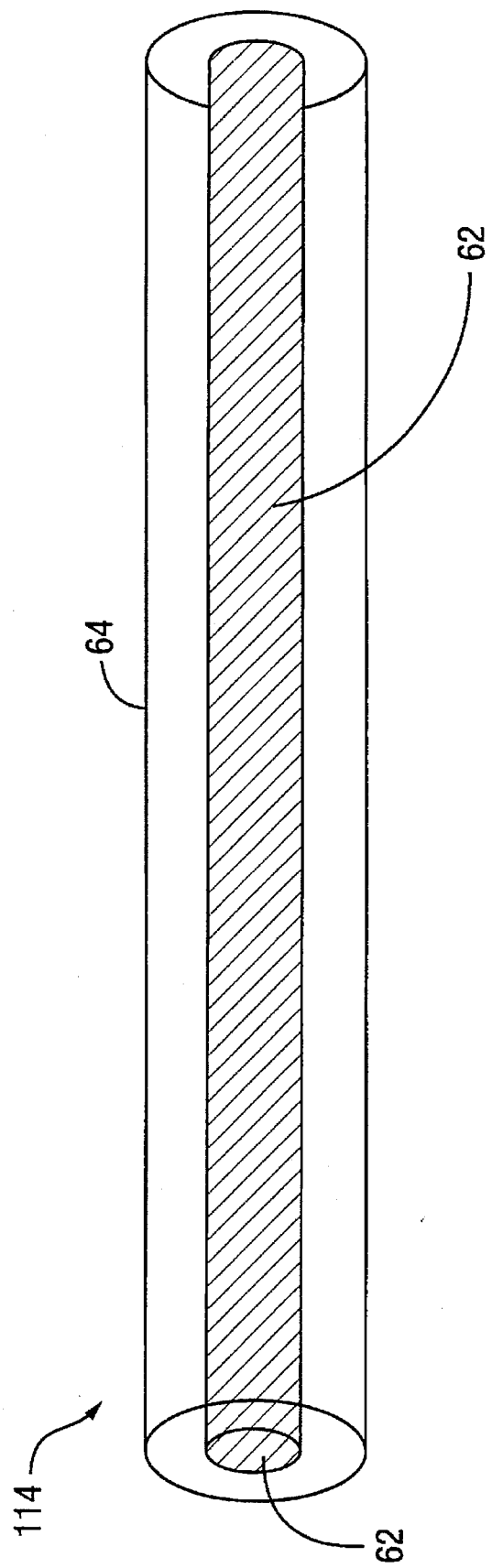
FIG. 17 illustrates a combined laser fiber optic and ultrasound transducer according to the present invention.

Ultrasound transducer 64 and laser fiber optic 62 may be combined as shown in FIG. 17. In this embodiment, fiber optic 62 is inserted through a hole in ultrasound transducer 64. Fiber optic 62 and ultrasound transducer 64 are held together firmly. Depending on the thermal therapy means selected, different types and frequencies of ultrasound transducer 64 may be used to yield both an adequate ultrasound detection range and an appropriate spatial resolution. Also, different types and diameters of fiber optic 62 may be utilized to achieve desired thermal energy deposit in tissues.

During patient treatment, the Doppler ultrasound signals contain not only the desired motion information created by heat due to a thermal modality such as a laser, but also contain undesirable artifacts introduced by tissue background motion. The background motion includes the tissue motion caused by heart beat, by lung respiration, by movement of patient's body, as well as movement of the combined ultrasound/laser transducer. The artifacts can be suppressed effectively by subtracting the ultrasound signal at a specific range gate designated as a reference gate from the ultrasound signals at different range gates. This is because the background motion creates similar artifacts at different range gates (i.e. different tissue depths). The middle range gate can be used as the reference range gate.

Figure 18:
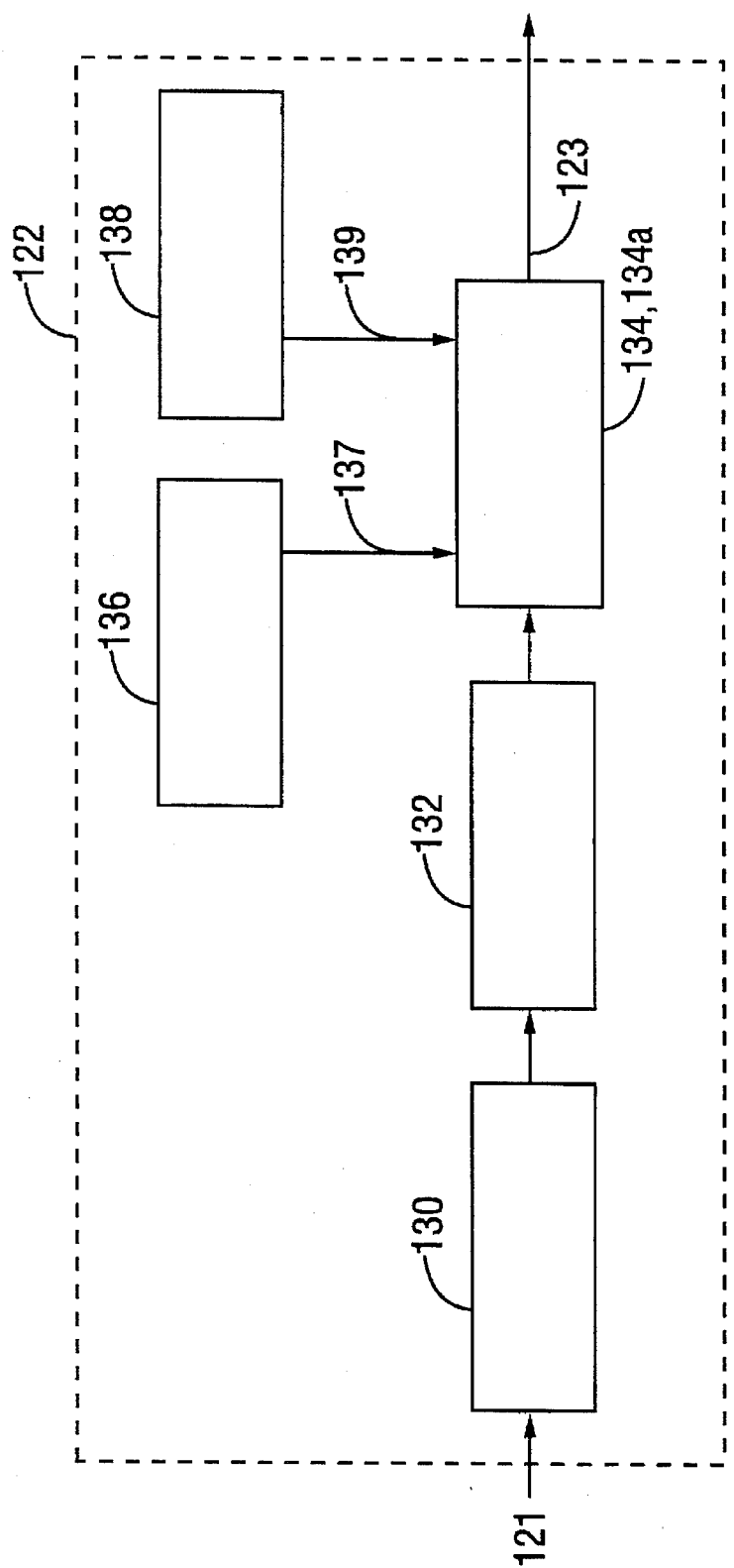
FIG. 18 is a block diagram of a tissue background signal elimination module for the apparatus shown in FIG. 16.

The detailed structure of the Tissue Background Signal Elimination Module is illustrated in FIG. 18. A digital infinite-duration impulse response (IIR) lowpass filter 130 filters the digital Doppler ultrasound signals 121. Filter 130 preferably has a very sharp cutoff frequency at 50 Hz to eliminate any frequencies higher than 50 Hz that remain in the Doppler signals after being filtered by analog lowpass filters 86$a$ in Doppler detector 60$b$. After the suppression of artifacts using the reference range gate, residual artifacts may remain in the ultrasound signals, which can effectively be removed by digital signal filtering. Two digital IIR bandstop filters 134 and 134$a$ are needed. One of the filters 134 eliminates the frequencies corresponding to the tissue motion synchronizing with the heart beat activity of the patient. The heart rate and heart activity signals (electrocardiogram, or ECG for short) 137 are provided by heart activity monitor 136. The other filter 134$a$ excludes the frequencies due to the tissue motion synchronizing with the lung respiration of the patient. The respiration rate along with respiration activity signals 139 are supplied by respiration activity monitor 138.

Figure 19:
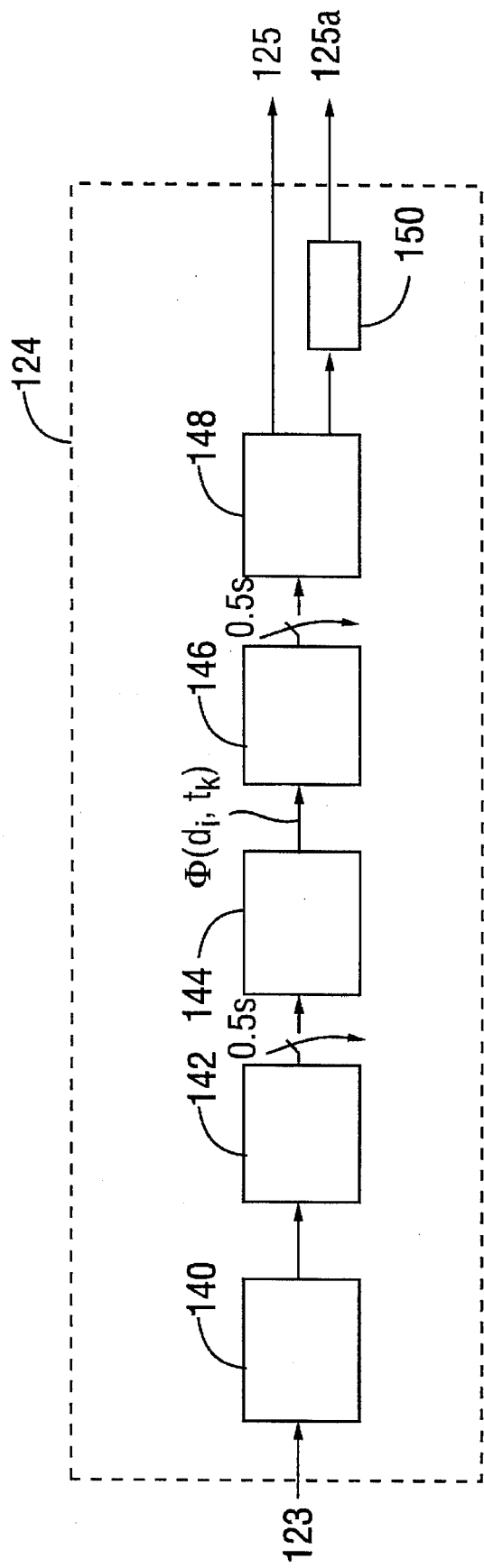
FIG. 19 is a block diagram of a Doppler signal processing module for the apparatus shown in FIG. 16.

The N Tissue Background Signal Elimination Modules 122 output N pairs of background-motion-free I and Q Doppler ultrasound signals 123 to the N identical Doppler Signal Processing Modules 124, the detailed structure of which is illustrated in FIG. 19. A third-order moving average algorithm 140 is employed to smooth the background motion-free I and Q Doppler ultrasound signals 123. The smoothed samples are sent to sample buffer 142, which can hold 512 samples. Buffer 142 is filled every 0.5 seconds. Once filled, buffer 142 sends 512 samples to ultrasound phase calculator 144 and empties buffer 142 to hold the incoming 512 samples. The buffer operation repeats every 0.5 second. Ultrasound phase calculator 144 computes instantaneous ultrasound phase according to:

$$\Phi(d_i, t_k) = \tan^{-1}(Q(d_i,t_k)/I(d_i,t_k)) \quad (20)$$

$$(i=1, 2, \ldots, N; k=1, 2, \ldots 512; t_k=\text{sampling time})$$

where $I(d_i,t_k)$ and $Q(d_i,t_k)$ are smoothed Doppler quadrature I and Q signals.

The computed instantaneous ultrasound phase data are sent to data buffer 146, which can hold 512 phase data. Once filled with 512 data in 0.5 seconds, data buffer 146 sends the phase data to power spectrum analyzer 148. Like sample buffer 142, data buffer 146 also empties itself periodically for upcoming phase data. Power spectrum analyzer 148 performs fast Fourier transform (FFT) on the ultrasound phase data. This results in a power spectrum of the phase signals describing strength of each Doppler shift frequency component during the 0.5 second period of time.

There are 512 Doppler shift frequency components, from 0 Hz to 50 Hz, with an equal frequency interval (frequency resolution) of 0.098 Hz (50/512 Hz). The Doppler shift frequency that has the most strength is found, which is then used as a dominant Doppler shift frequency representing the dominant motion velocity at a range gate. Integrator 150 sums all of the dominant Doppler shift frequencies up to the present sampling time. As a result, an accumulated dominant Doppler shift frequency 125a is obtained.

Figure 20:
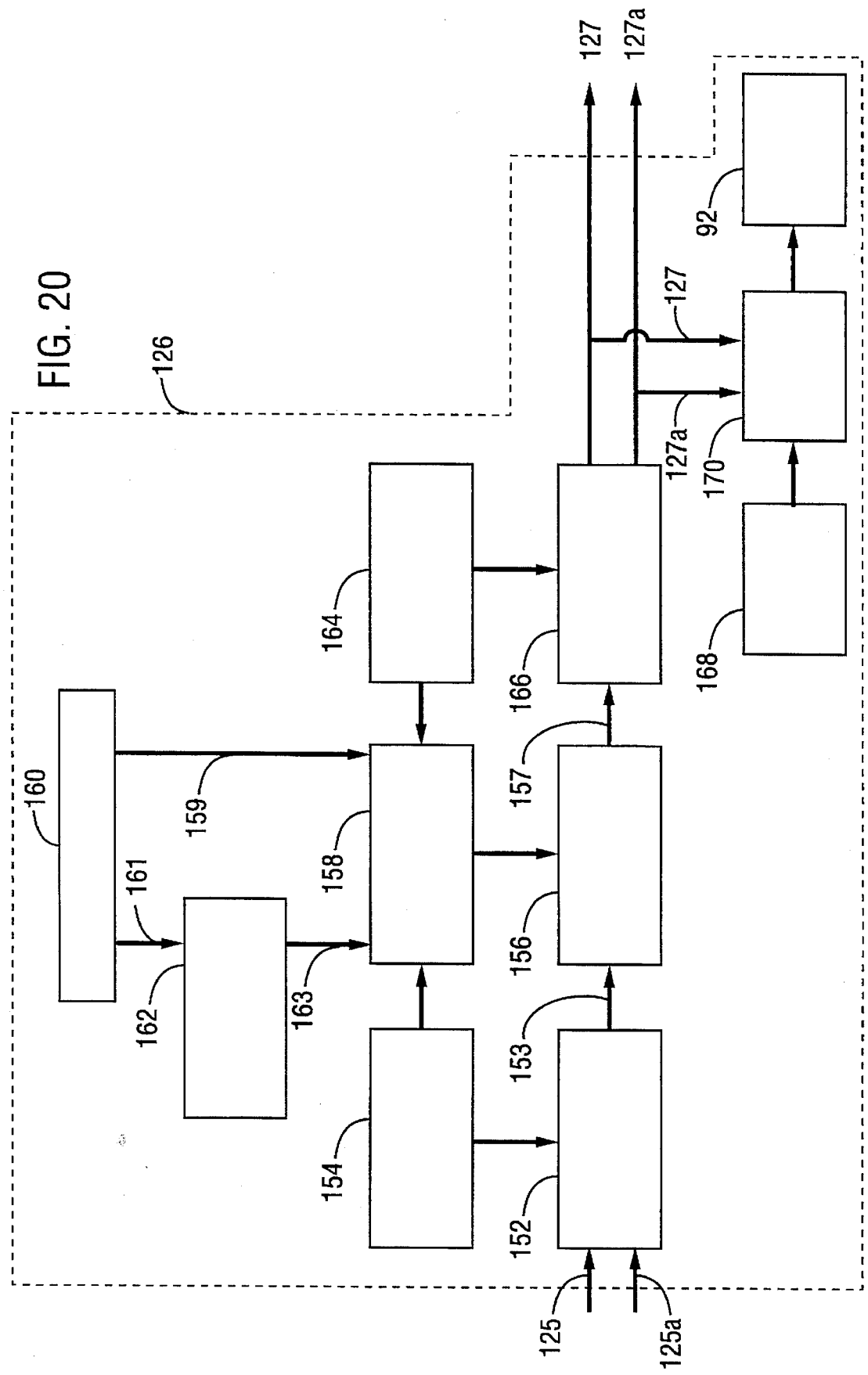
FIG. 20 is a block diagram of a tissue temperature and thermal damage determination module for the apparatus shown in FIG. 16.

N current dominant Doppler shift frequencies 125 and N accumulated dominant Doppler shift frequencies 125a are outputted to N identical Tissue Temperature and Thermal Damage Determination Modules 126, the detailed structure of which is illustrated in FIG. 20. This module is in essence a rule-based fuzzy logic system that correlates current dominant Doppler shift frequency and accumulated Doppler shift frequency at a range gate to the tissue temperature and tissue thermal damage in the tissue depth corresponding to the range gate.

The fuzzy logic system technology (Klir, G. J. and Folger, T. A. (1988), "Fuzzy sets, uncertainty, and information," Prentice Hall) has been recognized by IEEE (The Institute of Electrical and Electronics Engineers) as one of the three key information processing technologies. The basis of fuzzy logic systems is a fuzzy set (Zadeh, L. A., "Fuzzy sets," *Information and Control*, vol. 8, pp. 338–353 (1965)) that describes the membership of an object by a number between 0 and 1, as opposed to either 0 or 1 ("member" or "nonmember") as in classical set theory. For example, one fuzzy set might be "young." One might define "young" as follows: 10 years old is "young" with membership 1, 30 years old is "young" with membership 0.45, and 50 years old is "young" with membership 0.1. That is, everybody is "young" to a degree.

Fuzzy logic systems employ fuzzy set theory to emulate human expert knowledge and experience, and to process information involving uncertainty, ambiguity and contradiction. There have been many successful applications of fuzzy logic systems, particularly in the area of control, modeling (correlation) and pattern recognition. See Lee, C. C., "Fuzzy logic in control systems: fuzzy logic controller," *IEEE Transactions on Systems, Man and Cybernetics*, vol. 20, pp. 404–435 (1990); Ying, H., McEachern, M., Eddleman, D., Sheppard, L. C., "Fuzzy control of mean arterial pressure in postsurgical patients with sodium nitroprusside infusion," *IEEE Transactions on Biomedical Engineering*, vol. 39, pp. 1060–1070 (1992), the disclosures of which are herein incorporated by reference.

The module shown in FIG. 20 is a typical fuzzy logic system. It consists of fuzzification procedure 152, fuzzy logic and fuzzy inference 156, and defuzzification procedure 166. The current dominant Doppler shift frequency 125 and accumulated dominant Doppler shift frequency 125a are fuzzified in block 152 according to the fuzzy sets on dominant Doppler shift frequency and accumulated dominant Doppler shift frequency, respectively, defined in block 154. The fuzzy sets on dominant Doppler shift frequency 154 are trapezoidal shaped and are predefined with names like "very high," "high," "medium," "low," "very low," and "extremely low." The fuzzy sets cover the entire range of dominant Doppler shift frequencies, which is 0 to 50 Hz. The fuzzy sets on accumulated dominant Doppler shift frequency 154 are also trapezoidal shaped and are predefined with names like "very large," "large," "medium," "small," "very small," and "extremely small." The resulting fuzzy inputs 153 are linguistically related to tissue temperature and thermal damage by predefined fuzzy correlation rules 158, which are executed in block 156 in the form:

IF current dominant Doppler shift frequency at i-th range gate is "high"

AND accumulated dominant Doppler shift frequency at i-th range gate is "very large"

THEN tissue temperature at $d_i$ is "high"

AND tissue thermal damage at $d_i$ is "highly likely" irreversible.

Here "high" is a fuzzy set on tissue thermal temperature and "highly likely" is a fuzzy set on tissue thermal damage (both are predefined in "fuzzy set on tissue temperature and thermal damage" (block 164)). Other fuzzy sets are "very high," "near 100° C.," "modest," and "low" to cover entire tissue temperature range; and "certainly," "likely," "modestly likely" and "not likely" for describing tissue thermal damage. The fuzzy sets defined in blocks 159 and 164 are used in block 158 to form the fuzzy correlation rules.

Histologically speaking, a tissue damage in living animals is classified as one of two states: irreversible damage or reversible damage. Irreversible damage is permanent damage, which is the objective of thermal therapy. Reversible damage is temporary damage and the tissue will recover to its normal state after a period of time.

A set of such fuzzy correlation rules are predefined in 158 to cover all possible situations on tissue temperature and thermal damage. For a treatment, a subset of the rules is chosen for use. The selection is based on information from the lesion site 161 (e.g. in the liver, in the brain or in the heart, etc.) and laser system (laser type, different fiber optics, etc.—laser system information 159) given by the user ("user inputs" 160) before the thermal therapy is begun. Tissue characteristics knowledge base 162 transfers lesion site information 161 to tissue characteristics 163 in block 162 and sends them to fuzzy correlation rules 158 as the criteria of selecting the rules.

In module 126, all of the chosen fuzzy correlation rules are executed in parallel simultaneously. The fuzzy logic AND in each rule is computed using Zadeh fuzzy logic AND (min), and fuzzy logic OR between rules (the relationship between rules is OR) is calculated by Zadeh OR (max) ("fuzzy logic and fuzzy inference" 156). See Zadeh, L. A., "Fuzzy sets," *Information and Control*, vol. 8, pp. 338–353 (1965), the disclosure of which is herein incorporated by reference. Furthermore, the commonly used Mamdani's minimum inference method is used to infer in each of the rules the fuzzy sets in THEN part from the fuzzy sets in IF part ("fuzzy logic and fuzzy inference" 156). See Mizumoto, M., "Fuzzy Controls under Various Fuzzy Reasoning Methods," *Information Sciences*, vol. 45, pp. 129–151 (1988), the disclosure of which is herein incorporated by reference.

The execution of the rules generates fuzzy outputs on tissue temperature and thermal damage 157 with memberships between 0 and 1. Fuzzy outputs 157 need to be defuzzified (in "defuzzification" 166) to a crisp tissue temperature and a crisp likelihood of thermal damage status in terms of irreversible damage. This can be carried out by using the popular centroid defuzzifier that computes weighted average on the fuzzy outputs 157 with corresponding memberships. For tissue temperature, the result of the defuzzification 166 is a crisp tissue temperature between a few hundred degrees Celsius (the actual temperature range is application dependent). For thermal damage, the result is a number between 0 and 1 expressing the likelihood of irreversible damage. A threshold of 0.5 is utilized to generate 0 (reversible tissue damage) or 1 (irreversible tissue damage).

N tissue temperatures 127 and N thermal damage states 127a are sent to pseudo-color display processor 170. User-desired tissue temperature and thermal damage profile 168 is also fed into processor 170. Processor 170 produces user-predefined color graphics according to information received. The graphics are displayed in real-time on graphic color monitor 92a. The displayed information can be used by a human operator of a thermal modality to realize manual feedback control of the extent and geometry of tissue thermal damage in thermal therapy.

It has been proved theoretically that a fuzzy logic system like this module 126 can correlate system inputs to system outputs as accurately as desired, no matter how complex the correlation is. See Ying, H., "Sufficient Conditions on General Fuzzy Systems as Function Approximations," *Automatica*, vol. 30, pp. 521–525 (March 1994). This conclusion also holds for the Laser Control Module 128, which is a fuzzy logic system as well.

Figure 21:
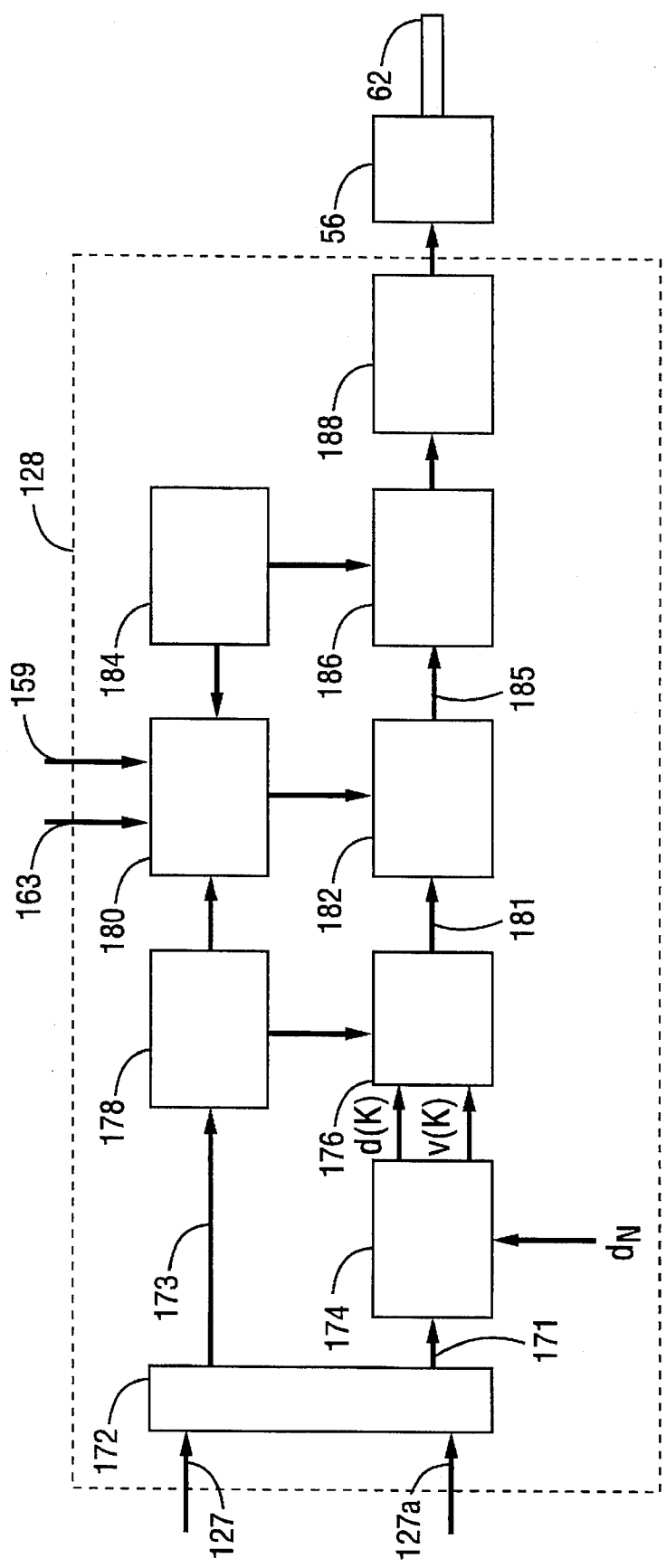
FIG. 21 is a block diagram of a laser control module for the apparatus shown in FIG. 16.

For real-time control of thermal therapy according to the results of Doppler ultrasound evaluation, N tissue temperature profiles 127 and N tissue thermal damage profiles 127a are sent to Laser Control Module 128 as feedback signals. The detailed structure of Laser Control Module 128 is illustrated in FIG. 21. Module 128 is similar to a typical fuzzy logic controller, whose structure is similar to Tissue Temperature and Thermal Damage Determination Module 126, although the two modules are for quite different purposes. Tissue damage front determiner 172 finds the range gate which represents the current tissue irreversible thermal damage front 171. Once found, the front along with the corresponding tissue temperature 173 are used as feedback signals for control module 128.

Without losing generality, suppose the user wants to achieve irreversible tissue thermal damage up to tissue depth $d_N$. Assume the tissue thermal damage status indicates that the current irreversible tissue damage front 171 is at $d_n$, where $1 < n \leq N$. If n=N, the laser should be turned off and the treatment is finished. Otherwise, laser modulation parameters need to be adjusted to cause more irreversible thermal damage so that $d_n$ can be equal to $d_N$.

Inputs calculator 174 calculates the input variables:

$$d(k) = d_N - d_n(k) \quad (20)$$

$$v(k) = d(k-1) - d(k). \quad (21)$$

where k is a positive integer representing sampling time. Increase of k by one is meant increase of 0.5 seconds of time. Values d(k) and v(k), defined in block 178, are fuzzified in the "fuzzification" block 176. As in module 126, trapezoidal fuzzy sets, such as "near zero," "small," "medium," "large" and "very large," are used for d(k) and v(k). Current tissue temperature at $d_n$ 173 is fuzzified in the "fuzzification" block 176 by the same fuzzy sets on tissue temperature 164 as those defined in the Tissue Temperature and Thermal Damage Module 126. The results of the fuzzification are fuzzy inputs 181, which will be used with fuzzy control rules 180 in block 182. Fuzzy sets defined in blocks 178 and 184 are used to form fuzzy control rules in block 180.

Fuzzy control rules 180 linguistically describe the strategy of changing laser modulation parameters based on the fuzzified d(k), v(k) and tissue temperature (fuzzy inputs 181). Laser system information 159 and tissue characteristics 163 from module 126 are input to select a subset of fuzzy control rules from fuzzy control rules 180. Laser modulation parameters are different for different types of lasers, and hence fuzzy sets on laser modulation parameters 184 are different. As an example, if one uses a diode laser as the thermal therapy modality, then the drive current can be used as a laser modulation parameter. Output power of a diode laser increases linearly with drive current once drive current is above a small laser threshold. See Hecht, J., "Understanding Lasers: An Entry-Level Guide," IEEE Press, (New York 1992).

Suppose we use a diode laser. Then, we define the fuzzy sets 184 on drive current as "very small," "small," "medium," "large," "very large" and "huge." A fuzzy control rule in block 180 will look like:

IF d(k) is "large" AND v(k) is "small" AND tissue temperature at $d_n$ is "low" THEN drive current should be "very large."

Given a patient, control rules are selected according to tissue characteristics 163 and laser system information 159 that are provided by Tissue Temperature and Thermal Damage Module 126. The fuzzy control rules are executed in parallel by the same fuzzy logic and fuzzy inference method (block 182) as those used in Tissue Temperature and Thermal Damage Module 126. The resultant fuzzy sets on drive current (fuzzy outputs 185) with memberships are defuzzified in block 186 by a centroid defuzzifier to yield a crisp amount of drive current. The current is sent to laser modulator 188 to regulate the thermal output power of laser 56 connected to fiber optic 62.

Further modifications and alternative embodiments of this invention will be apparent to those skilled in the art in view of this description. For example, the laser used as an exemplary thermal modality in FIGS. 2, 2a, 17 and 22 may be replaced with other suitable thermal therapy instruments, such as thermistors, electromagnetic wave or ultrasound. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A method for ultrasonic Doppler monitoring of the extent and geometry of damage to a tissue resulting from treatment with a thermal modality, comprising the steps of:

providing an echo-Doppler transmitter/receiver coupled to a transducer;

treating a tissue with a thermal modality;

emitting ultrasonic waves from said transducer toward the region of a tissue receiving thermal treatment;

receiving echoes from the thermally treated tissue;

converting the echoes to electrical echo signals, said echo signals each containing a phase vector indicating motion and echogenicity in the tissue relative to the transducer at a plurality of tissue depths;

deriving x and y components of the phase vector of each echo signal as functions of range and time;

outputting pairs of in-phase and quadrature-phase (I and Q) Doppler signals; and evaluating said I and Q Doppler signals to determine the extent and geometry of tissue damage resulting from said thermal treatment.

2. The method of claim 1, wherein said treating step comprises:

providing a laser coupled to an optical fiber;

directing a laser beam from said laser through said optical fiber into said tissue;

providing an ultrasonic transducer probe coupled to said echo-Doppler transmitter/receiver; and angling said transducer probe relative to said optical fiber so that said laser beam emitted from said optical fiber and a sound beam emitted from said transducer probe will intersect below the surface of said tissue being treated with said laser.

3. The method of claim 1, wherein said treating step comprises:

providing a laser coupled to an optical fiber:

providing an ultrasonic transducer coupled to said echo-Doppler transmitter/receiver, wherein said transducer has a hollow core with said optical fiber disposed therein so that a laser beam projected through said optical fiber is substantially collinear with a sound beam emitted from said ultrasonic transducer.

4. The method of claim 1, wherein said evaluating step comprises:

eliminating background signals in I and Q Doppler signals to produce background-motion-free I and Q Doppler signals;

processing said background-motion-free I and Q Doppler signals to produce current dominant shift Doppler frequencies and accumulated dominant Doppler frequencies;

processing said current dominant shift Doppler frequencies and accumulated dominant Doppler frequencies to produce tissue temperature readings at multiple tissue depths and readings indicating the extent and geometry of tissue thermal damage at multiple tissue depths;

determining a tissue irreversible damage front from said readings indicating extent and geometry of tissue thermal damage; and comparing a current tissue irreversible damage front to a user-desired tissue irreversible damage front to produce a difference signal and using the difference signal as well as the temperature of the current tissue irreversible damage front to produce a modulation signal for controlling the output of said thermal modality.

5. Apparatus for ultrasonic Doppler monitoring of the extent and geometry of damage due to thermal treatment of a living tissue, comprising:

a thermal modality for applying thermal treatment to a living tissue;

an echo-Doppler transmitter/receiver for emitting ultrasonic waves toward the region of said living tissue receiving thermal treatment, for receiving echoes from the treated tissue, and for converting the echoes to electrical signals, said electrical signals each containing a phase vector indicating motion and echogenicity in the tissue relative to the transducer at a plurality of tissue depths;

echo-signal processing means coupled to said echo-Doppler transmitter/receiver for deriving x and y components of the phase vector of each echo signal as functions of range and time and for outputting multiple pairs of I and Q Doppler signals; and evaluating means coupled to said echo-signal processing means for determining the extent and geometry of tissue damage resulting from said thermal treatment.

6. The apparatus of claim 5, wherein said echo-signal processing means comprises:

a quadrature-phase detector coupled to said echo-Doppler transmitter/receiver for outputting x and y components of the phase vector;

a delayed-pulse generator coupled to said echo-Doppler transmitter/receiver for producing range-gate pulses;

a dual sample/hold circuit coupled to said quadrature-phase detector and said pulse generator for receiving x and y signals and range-gate pulses and for producing multiple pairs of I and Q Doppler signals; and a lowpass filter coupled to receive said I and Q Doppler signals from said dual sample/hold circuit.

7. The apparatus of claim 5, further comprising:

a transducer probe coupled to said echo-Doppler transmitter/receiver, said transducer probe terminating in a probe tip.

8. The apparatus as recited claim 7, wherein said thermal modality comprises a laser coupled to an optical fiber.

9. The apparatus as recited in claim 8, wherein said transducer probe is angled relative to said optical fiber so that a laser beam emitted from said laser through said optical fiber and a sound beam emitted from said transducer will intersect below the surface of a tissue being treated with said laser.

10. The apparatus as recited in claim 8, wherein said transducer has a hollow core with said optical fiber disposed therein so that a laser beam projected through said optical fiber is substantially collinear with a sound beam emitted from said ultrasonic transducer.

11. The apparatus of claim 5, wherein said evaluating means further comprises:

means coupled to said Doppler detector for receiving I and Q Doppler signals and for eliminating background signals in said I and Q signals to produce background-motion-free I and Q Doppler signals;

means for processing said background-motion-free I and Q Doppler signals to produce current dominant shift Doppler frequencies and accumulated dominant Doppler frequencies;

means for processing said current dominant shift Doppler frequencies and accumulated dominant Doppler frequencies to produce tissue temperature readings at multiple tissue depths and readings indicating the extent and geometry of tissue thermal damage;

means for determining a tissue irreversible damage front from said readings indicating extent and geometry of tissue thermal damage; and means for comparing a current tissue irreversible damage front to a user-desired tissue irreversible damage front to produce a difference signal and using the difference signal as well as the temperature of the current tissue irreversible damage front to produce a modulation signal for controlling the output of said thermal modality.

* * * * *

UNITED STATES PATENT AND TRADEMARK OFFICE
CERTIFICATE OF CORRECTION

PATENT NO. : 5,657,760

DATED : August 19, 1997

INVENTOR(S) : Hao Ying and Craig J. Hartley

It is certified that error appears in the above-identified patent and that said Letters Patent is hereby corrected as shown below:

Title page, item [73], line 3, insert --Baylor College of Medicine, Houston, Texas--

Signed and Sealed this

Sixth Day of January, 1998

Attest:

BRUCE LEHMAN

*Attesting Officer*  *Commissioner of Patents and Trademarks*